(12) United States Patent
de Zambotti et al.

(10) Patent No.: US 11,804,301 B2
(45) Date of Patent: Oct. 31, 2023

(54) SYSTEMS AND METHODS INVOLVING PREDICTIVE MODELING OF HOT FLASHES

(71) Applicant: SRI International, Menlo Park, CA (US)

(72) Inventors: Massimiliano de Zambotti, Burlingame, CA (US); Fiona C. Baker, San Jose, CA (US); Mohamad Forouzanfar, Palo Alto, CA (US); Bhaskar Ramamurthy, Los Altos, CA (US); Laurie Menoud, San Francisco, CA (US)

(73) Assignee: SRI International, Menlo Park, CA (US)

( * ) Notice: Subject to any disclaimer, the term of this patent is extended or adjusted under 35 U.S.C. 154(b) by 543 days.

(21) Appl. No.: 16/503,064

(22) Filed: Jul. 3, 2019

(65) Prior Publication Data

US 2020/0013511 A1    Jan. 9, 2020

Related U.S. Application Data

(60) Provisional application No. 62/694,946, filed on Jul. 6, 2018.

(51) Int. Cl.
*G16H 50/20* (2018.01)
*G06N 7/01* (2023.01)
(Continued)

(52) U.S. Cl.
CPC ............... *G16H 50/20* (2018.01); *G06N 5/02* (2013.01); *G06N 7/01* (2023.01)

(58) Field of Classification Search
CPC .......... G16H 50/20; G06N 5/02; G06N 7/005; G06Q 50/20–26
(Continued)

(56) References Cited

U.S. PATENT DOCUMENTS 10,483,003 B1 * 11/2019 McNair .................. G16H 50/30
10,610,144 B2 *  4/2020 Eldardiry ............... G16H 50/20
(Continued)

FOREIGN PATENT DOCUMENTS

JP       201738924 A     2/2017

OTHER PUBLICATIONS

Avis NE, Crawford SL, Greendale G, et al. Duration of menopausal vasomotor symptoms over the menopause transition. JAMA internal medicine 2015; 175:531-9.
(Continued)

*Primary Examiner* — Neal Sereboff
(74) *Attorney, Agent, or Firm* — Dicke, Billig & Czaja, PLLC

(57) ABSTRACT

Embodiments in accordance with the present disclosure are directed to systems and methods for managing hot flashes and/or menopause symptoms. An example system includes sensor circuitry and logic circuitry. The sensor circuitry obtains a physical measurement associated with a user and communicates the physical measurement. The logic circuitry generates a predictive model that indicates a probability of the user having a hot flash at a date and time based on a plurality of input parameters, revises the probability based on the physical measurement using the predictive model, and communicates data indicative of an action in response to the revised probability being outside a threshold, such as providing cooling relief.

23 Claims, 15 Drawing Sheets

(51) Int. Cl.
*G06N 5/02* (2023.01)
*G06N 7/00* (2023.01)

(58) Field of Classification Search
USPC .......................................................... 705/2–3
See application file for complete search history.

(56) References Cited

U.S. PATENT DOCUMENTS

| | | | | |
|---|---|---|---|---|
| 2005/0222157 | A1* | 10/2005 | Wessel | A61K 31/498 514/249 |
| 2015/0320588 | A1* | 11/2015 | Connor | A61F 7/0085 607/107 |
| 2018/0315505 | A1* | 11/2018 | Itu | G16H 10/20 |
| 2019/0110950 | A1* | 4/2019 | Smith | G06F 1/163 |
| 2019/0282178 | A1* | 9/2019 | Volosin | A61B 5/0022 |

OTHER PUBLICATIONS

Gold EB, Colvin A, Avis N, et al. Longitudinal analysis of the association between vasomotor symptoms and race/ethnicity across the menopausal transition: Study of women's health across the nation. Am J Public Health 2006; 96:1226-35.

Woods NF, Mitchell ES, Landis C. Anxiety, hormonal changes, and vasomotor symptoms during the menopause transition. Menopause 2005; 12:242-5.

Kronenberg F. Hot flashes: epidemiology and physiology. Ann N Y Acad Sci 1990; 592:52-86; discussion 123-33. Abstract Only.

Freedman RR. Menopausal hot flashes: mechanisms, endocrinology, treatment. The Journal of steroid biochemistry and molecular biology 2014; 142:115-20.

Low DA, Hubing KA, Del Coso J, Crandall CG. Mechanisms of cutaneous vasodilation during the postmenopausal hot flash. Menopause 2011; 18:359-65.

Low DA, Davis SL, Keller DM, Shibasaki M, Crandall CG. Cutaneous and hemodynamic responses during hot flashes in symptomatic postmenopausal women Menopause 2008; 15:290-5.

El Khoudary SR, Thurston RC. Cardiovascular Implications of the Menopause Transition: Endogenous Sex Hormones and Vasomotor Symptoms. Obstet Gynecol Clin North Am 2018; 45:641-61. Abstract Only.

Thurston RC, El Khoudary SR, Tepper PG, et al. Trajectories of Vasomotor Symptoms and Carotid Intima Media Thickness in the Study of Women's Health Across the Nation. Stroke 2016; 47:12-7.

Thurston RC, Chang Y, Mancuso P, Matthews KA. Adipokines, adiposity, and vasomotor symptoms during the menopause transition: findings from the Study of Women's Health Across the Nation. Fertil Steril 2013; 100:793-800.

Thurston RC, El Khoudary SR, Sutton-Tyrrell K, et al. Vasomotor symptoms and lipid profiles in women transitioning through menopause. Obstet Gynecol 2012; 119:753-61.

Thurston RC, El Khoudary SR, Sutton-Tyrrell K, et al. Vasomotor symptoms and insulin resistance in the study of women's health across the nation. J Clin Endocrinol Metab 2012; 97:3487-94.

Trinder J, Waloszek J, Woods MJ, Jordan AS. Sleep and cardiovascular regulation. Pflugers Arch 2012; 463:161-8. Abstract Only.

Carrington MJ, Trinder J. Blood pressure and heart rate during continuous experimental sleep fragmentation in healthy adults. Sleep 2008; 31:1701-12.

Routledge FS, Dunbar SB, Higgins M, et al. Insomnia Symptoms Are Associated With Abnormal Endothelial Function. J Cardiovasc Nurs 2015.

Salles GF, Reboldi G, Fagard RH, et al. Prognostic Effect of the Nocturnal Blood Pressure Fall in Hypertensive Patients: The Ambulatory Blood Pressure Collaboration in Patients With Hypertension (ABC-H) Meta-Analysis. Hypertension 2016; 67:693-700.

Baker FC, de Zambotti M, Colrain IM, Bei B. Sleep problems during the menopausal transition: prevalence, impact, and management challenges. Nat Sci Sleep 2018; 10:73-95.

Kravitz HM, Joffe H. Sleep during the perimenopause: a SWAN story. Obstet Gynecol Clin North Am 2011; 38:567-86.

Ohayon MM. Severe hot flashes are associated with chronic insomnia. Arch Intern Med 2006; 166:1262-8.

De Zambotti M, Colrain IM, Javitz HS, Baker FC. Magnitude of the impact of hot flashes on sleep in perimenopausal women. Fertil Steril 2014; 102:1708-15.

Joffe H, Crawford S, Economou N, et al. A Gonadotropin-Releasing Hormone Agonist Model Demonstrates that Nocturnal Hot Flashes Interrupt Objective Sleep. Sleep 2013; 36:1977-85.

Freedman RR, Roehrs TA. Effects of REM sleep and ambient temperature on hot flash-induced sleep disturbance. Menopause 2006; 13:576-83. Abstract Only.

Gast GC, Grobbee DE, Pop VJ, et al. Menopausal complaints are associated with cardiovascular risk factors. Hypertension 2008; 51:1492-8.

James GD, Sievert LL, Flanagan E. Ambulatory blood pressure and heart rate in relation to hot flash experience among women of menopausal age. Ann Hum Biol 2004; 31:49-58. Abstract Only.

Gast GC, Pop VJ, Samsioe GN, et al. Vasomotor menopausal symptoms are associated with increased risk of coronary heart disease. Menopause 2011; 18:146-51. Abstract Only.

De Zambotti M, Colrain I, Sassoon S, Nicholas C, Trinder J, Baker F. Vagal withdrawal during hot flashes occurring in undisturbed sleep. Menopause 2013; 20:1147-53.

Thurston RC, Matthews KA, Chang Y, et al. Changes in heart rate variability during vasomotor symptoms among midlife women. Menopause 2016; 23:499-505.

Tuomikoski P, Haapalahti P, Sarna S, Ylikorkala O, Mikkola TS. Vasomotor hot flushes and 24-hour ambulatory blood pressure in normotensive women: A placebo-controlled trial on postmenopausal hormone therapy. Annals of medicine 2010; 42:334-43. Abstract Only.

Sherwood A, Allen MT, Fahrenberg J, Kelsey RM, Lovallo WR, van Doornen LJ. Methodological guidelines for impedance cardiography. Psychophysiology 1990; 27:1-23.

Baker F, Willoughby AR, Sassoon S, Colrain IM, de Zambotti M. Insomnia in women approaching menopause: beyond perception. Psychoneuroendocrinology 2015; 60:96-104.

Sassoon S, de Zambotti M, Colrain I, Baker F. Association between personality traits and DSM-IV diagnosis of insomnia in peri- and postmenopausal women. Menopause 2014; 21:602-11.

Soules M, Sherman S, Parrott E, et al. Executive summary: Stages of Reproductive Aging Workshop (STRAW). Climacteric 2001; 4:267-72. Abstract Only.

Beck AT, Steer RA, Brown GK. Manual for the Beck Depression Inventory, 2nd ed. San Antonio, TX: The Psychological Corporation., 1996. Abstract Only.

Buysse DJ, Reynolds CF, 3rd, Monk TH, Berman SR, Kupfer DJ. The Pittsburgh Sleep Quality Index: a new instrument for psychiatric practice and research. Psychiatry Res 1989; 28:193-213.

Nicassio PM, Mendlowitz DR, Fussell JJ, Petras L. The phenomenology of the pre-sleep state: the development of the pre-sleep arousal scale. Behav Res Ther 1985; 23:263-71. Abstract Only.

Berry RB, Brooks R, Gamaldo CE, Harding SM, Lloyd RM, Marcus CL and Vaughn BV. The AASM Manual for the Scoring of Sleep and Associated Events: Rules, Terminology and Technical Specifications. American Academy of Sleep Medicine, 2015.

Castiglioni P, Parati G, Omboni S, et al. Broad-band spectral analysis of 24 h continuous finger blood pressure: comparison with intra-arterial recordings. Clin Sci (Lond) 1999; 97:129-39.

Sherwood A, Royal S, Hutcheson J, Turner J. Comparison of impedance cardiographic measurements using band and spot electrodes. Psychophysiology 1992; 29:734-41. Abstract Only.

Forouzanfar M, Baker FC, de Zambotti M, McCall C, Giovangrandi L, Kovacs GTA. Toward a better noninvasive assessment of preejection period: A novel automatic algorithm for B-point detection and correction on thoracic impedance cardiogram. Psychophysiology 2018; 55:e13072.

Cacioppo JT, Berntson GG, Binkley PF, Quigley KS, Uchino BN, Fieldstone A. Autonomic cardiac control. II. Noninvasive indices and basal response as revealed by autonomic blockades. Psychophysiology 1994; 31:586-98.

(56) References Cited

OTHER PUBLICATIONS

Freedman RR. Laboratory and ambulatory monitoring of menopausal hot flashes. Psychophysiology 1989; 26:573-9. Abstract Only.
Savard MH, Savard J, Caplette-Gingras A, Ivers H, Bastien C. Relationship between objectively recorded hot flashes and sleep disturbances among breast cancer patients: investigating hot flash characteristics other than frequency. Menopause 2013; 20:997-1005.
Thurston RC, Hernandez J, Del Rio JM, De La Torre F. Support Vector Machines to improve physiologic hot flash measures: application to the ambulatory setting. Psychophysiology 2011; 48:1015-21.
Wang D, Tang J, Liu S, Huang J. Carbohydrate Microarrays Identify Blood Group Precursor Cryptic Epitopes as Potential Immnunological Targets of Breast Cancer. Journal of Immunology Research 2015; 1-10.
Davies RJ, Belt PJ, Roberts SJ, Ali NJ, Stradling JR. Arterial blood pressure responses to graded transient arousal from sleep in normal humans. J Appl Physiol (1985) 1993; 74:1123-30. Abstract Only.
Morgan BJ, Crabtree DC, Puleo DS, Badr MS, Toiber F, Skatrud JB. Neurocirculatory consequences of abrupt change in sleep state in humans. J Appl Physiol (1985) 1996; 80:1627-36. Abstract Only.
Tamisier R, Weiss JW, Pepin JL. Sleep biology updates: Hemodynamic and autonomic control in sleep disorders. Metabolism 2018; 84:3-10. Abstract Only.
Chouchou F, Pichot V, Pepin JL, et al. Sympathetic overactivity due to sleep fragmentation is associated with elevated diurnal systolic blood pressure in healthy elderly subjects: the PROOF-SYNAPSE study. Eur Heart J 2013; 34:2122-31, 31a.
Taylor KS, Murai H, Millar PJ, et al. Arousal From Sleep and Sympathetic Excitation During Wakefulness. Hypertension 2016; 68:1467-74.
Trinder J, Allen N, Kleiman J, et al. On the nature of cardiovascular activation at an arousal from sleep. Sleep 2003; 26:543-51.
De Zambotti M, Trinder J, Javitz H, Colrain IM, Baker FC. Altered nocturnal blood pressure profiles in women with insomnia disorder in the menopausal transition. Menopause 2017; 24:278-87.
Forouzanfar M, Zambotti M, Goldstone A, Baker FC. Automatic Detection of Hot Flash Occurrence and Timing from Skin Conductance Activity. Conf Proc IEEE Eng Med Biol Soc 2018;2018:1090-3.
Sturdee DW, Wilson KA, Pipili E, Crocker AD. Physiological aspects of menopausal hot flush. Br Med J 1978; 2:79-80.
Kato T, Montplaisir JY, Lavigne GJ. Experimentally induced arousals during sleep: a cross-modality matching paradigm. J Sleep Res 2004; 13:229-38.
Freedman RR, Woodward S, Sabharwal SC. Alpha 2-adrenergic mechanism in menopausal hot flushes. Obstet Gynecol 1990; 76:573-8. Abstract Only.
Zepelin H, McDonald CS, Zammit GK. Effects of age on auditory awakening thresholds. J Gerontol 1984; 39:294-300. Abstract Only.
Halasz P, Terzano M, Parrino L, Bodizs R. The nature of arousal in sleep. J Sleep Res 2004; 13:1-23.
Rechtschaffen A, Hauri P, Zeitlin M. Auditory awakening thresholds in REM and NREM sleep stages. Perceptual and motor skills 1966; 22:927-42. Abstract Only.
Sagot JC, Amoros C, Candas V, Libert JP. Sweating responses and body temperatures during nocturnal sleep in humans. Am J Physiol 1987; 252:R462-70. Abstract Only.
Franco OH, Muka T, Colpani V, et al. Vasomotor symptoms in women and cardiovascular risk markers: Systematic review and meta-analysis. Maturitas 2015; 81:290-304.
Sassarini J, Lumsden MA. Vascular function and cardiovascular risk factors in women with severe flushing. Maturitas 2015; 80:379-83.
Gerber LM, Sievert LL, Warren K, Pickering TG, Schwartz JE. Hot flashes are associated with increased ambulatory systolic blood pressure. Menopause 2007; 14:308-15. Abstract Only.
Jackson EA, El Khoudary SR, Crawford SL, et al. Hot Flash Frequency and Blood Pressure: Data from the Study of Women's Health Across the Nation. J Womens Health (Larchmt) 2016; 25:1204-9.
Brown DE, Sievert LL, Morrison LA, Rahberg N, Reza A. Relationship between hot flashes and ambulatory blood pressure: the Hilo women's health study. Psychosom Med 2011; 73:166-72.
Baker FC, Forouzanfar M, Goldstone AM, Claudatos SA, Javitz Harold, Trinder John, de Zambotti M. Changes in heart rate and blood pressure during nocturnal hot flashes associated with and without awakenings, Sleep, vol. 42, Issue 11, Nov. 2019, 175.
EPO. Extended European Search Report dated Nov. 19, 2019, for related European Patent Application No. 19184522.1, 9 pages.
Gibson, et al., "Cortisol dysregulation is associated with daily diary-reported hot flashes among midlife women", Clinical Endocrinology, Blackwell Scientific Publications, Oxford, GB, vol. 85, No. 4, Apr. 26, 2016, pp. 645-651.
European Communication pursuant to Article 94(3) EPC for related European Patent Application No. 19184522.1 dated Nov. 29, 2022.
Japanese Notice of Refusal dated Feb. 21, 2023 for Japanese Patent Application No. 2019-126419.

\* cited by examiner

SYSTEMS AND METHODS INVOLVING PREDICTIVE MODELING OF HOT FLASHES

OVERVIEW

Hot flashes, also called vasomotor symptoms or hot flush, are a sensation of heat, sweating, flashing, anxiety, and chills that generally last between three to ten minutes. Hot flashes are common in women approaching menopause and post-menopause. For example, it is estimated that up to eighty percent of women reaching menopause are plagued by hot flashes, which can persist for several years post-menopause. Some women have hot flashes hourly or daily, and others report only one or two per week. Additionally, hot flashes are not limited to women approaching menopause or post-menopause. For example, women who have a hysterectomy and ovariectomy or women who are undergoing certain treatments for breast cancer may also experience frequent and severe hot flashes as one of their symptoms. Additionally, men may experience hot flashes when undergoing certain treatments, such as cancer related treatment.

Menopausal hot flashes occur in association with a shift in reproductive hormone levels, with an increase in follicle stimulating hormone and decrease in estradiol in the approach to menopause. This withdrawal of estrogen is hypothesized to impact the stability of the central thermoregulatory center in the brain, leading to the manifestation of hot flashes. Alteration in automatic nervous system controls may also be implicated in the manifestation of these vasomotor symptoms. Hot flashes negatively impact daytime functioning, work productivity, mood, and sleep, and are also linked with increased risk for cardiovascular disease in later life. Since hot flashes can persist for several years past menopause they potentially have a long-term negative influence on quality of life.

A distressing factor underlying hot flashes is that the sufferer has little control over them as hot flashes can seem to occur at random inconvenient times, and across the day and night, interfering with work, home, and sleep. Hot flashes can be eradicated with hormone therapy, but hormone therapy is not appropriate for everyone, whether due to risk profiles or personal preferences. Other non-hormonal prescription medications that can be effective include selective serotonin re-uptake inhibitors and gabapentin, but these treatments also have side-effects and are not for everyone. There are also non-pharmacological options which may focus on the negative consequences of hot flashes (e.g., discomfort due to sweating, irritation/anxiety due to the embarrassment of experiencing hot flashes in public or during work) as a single time point intervention after a hot flashes manifests.

SUMMARY OF THE INVENTION

The present invention is directed to overcoming the above-mentioned challenges and others related to managing hot flashes.

Various embodiments of the present disclosure are directed to systems, devices and methods thereof that can be used for managing hot flashes for a user by tracking hot flash occurrences over time and, based on the tracked data, generating a prediction model indicative of a likelihood of a hot flash at a particular time. The system allows users (e.g., hot flash sufferers) to comprehensively manage hot flashes, such as women with menopausal symptoms as they go through menopause, which can be used to make a decision together with their clinician about what treatment to consider. In specific embodiments, the system empirically track the occurrence, severity, triggers, and impact of hot flashes. For each specific user and/or users in general, there are specific biopsychosocial factors (e.g., stress, drinking hot beverages, eating spicy food, hot environments), physiological state, demography and behaviors that are associated with a greater probability of having a hot flash. The system can learn over time what biological, individual, and environmental factors trigger hot flashes and/or increase a probability of an occurrence of a hot flash and/or a severity of the hot flash, putting users in control of the management of their symptoms and optionally enabling the provision of cooling relief or other therapeutics in advance of, or coincident with, a suspected hot flash.

Specific embodiments are directed to a system including sensor circuitry and logic circuitry, such as a hot flash management system and/or a menopause management system. The sensor circuitry, which include a communication circuit, obtains a physical measurement associated with a user and communicates the physical measurement. The logic circuitry generates a predictive model that indicates a probability of the user having a hot flash at a date and time based on a plurality of input parameters, revises the probability based on the physical measurement using the predictive model, and communicates data indicative of an action in response to the revised probability being outside a threshold. In specific embodiments, the revised probability may indicate a severity or predicted severity of the hot flash, which may be based on or measured by perceived disturbance and/or impact of a multi-system functionality (e.g., hot flash related cardiovascular activation). For example, the system can quantify hot flashes severity in different ways, including but not limited to impact the hot flashes have on sleep. The revised probability being outside the threshold indicates that a hot flash is imminent (e.g., anticipated) and/or is predicted to occur at a particular time and date. Revising a probability, in this regard, includes or refers to determining or generating a numerical value associated with the likelihood of an occurrence of a hot flash for the user using the predictive model and the input parameters.

The physical measurement obtained by the sensor circuitry comprises a physiological signal, atmospheric measurement, motion data, and global position data, and the logic circuitry communicates data indicative of the action including communicating a message to the user to take the action to mitigate a hot flash. As an example, the sensor circuitry includes a wearable physiological sensor to sense a physiological signal from the user, such as skin conductance or skin temperature. The sensor circuitry additionally or alternatively includes another sensor to sense an atmospheric measurement.

The input parameters are indicative of or otherwise include hot flash factors for a user and/or other users. For example, the logic circuitry receives the plurality of input parameters that comprise reported hot flashes and timing information, schedule or calendar data, stress level, general mood, dietary information, exercise data, sleep data, health information, among other information and a combination thereof. The predictive model includes a plurality of sub-models that each indicate the probability of the user having the hot flash, each the plurality of sub-models being associated with a particular input parameter of the plurality of parameters and having an associated weight. For example, the sub-models include different patterns of hot flashes for the user based on the particular input parameter. The logic circuitry may revise the predictive model over time based on feedback data indicative of experienced hot flashes. The feedback data, in a specific embodiment, is indicative of a body location of the hot flash, verification of a hot flash occurring and/or indicative of a severity or impact of the hot flash. The feedback data may be actively provided by the user and/or obtained using the sensor circuitry.

The data communicated by the logic circuitry may include an instruction to activate cooling circuitry. The cooling circuitry has a communication circuit and heat transfer circuitry to provide cooling to the user in response to the instruction. In other embodiments and/or in addition, the logic circuitry provides an instruction to the sensor circuitry to adjust the physical measurement in response to the probability of the user having the hot flash being outside another threshold and within the threshold, as further described herein.

A number of embodiments can include a non-transitory computer-readable storage medium comprising instructions that when executed cause a processor circuit of a computing device to receive a plurality of input parameters indicative of hot flash factors for a user and other users, generate a predictive model that indicates a probability of the user having a hot flash at a date and time based on the plurality of input parameters, revise the probability based on a physical measurement of the user, received from the sensor circuitry, using the predictive model, and communicate data indicative of an action in response to the revised probability being outside a threshold, the action being based on prior user response. In specific embodiments, the communicated data is an instruction that activates cooling circuitry worn by the user, and in response to the activation, the cooling circuitry provides cooling to the user to mitigate or prevent an imminent or occurring hot flash. The computing device further generates another instruction to deactivate the cooling circuitry worn by the user in response to a further revised probability being within the threshold, the further revised probability being based on an additionally received physical measurement.

In a number of related embodiments, the instructions to generate the predictive model are executed to revise the predictive model based on additional input parameters received over time. For example, the predictive model can be dynamically updated over time based on additional input parameters and feedback data. The instructions may be further executed to provide an instruction to the sensor circuitry to adjust the physical measurement in response to the probability being outside another threshold and within the threshold, wherein the probability being outside the other threshold indicates a predicted hot flash for the user and being outside the threshold indicates an imminent hot flash for the user.

Various-related and more specific embodiments are directed to a system that includes sensor circuitry, logic circuitry, and cooling circuitry. The sensor circuitry, which includes a communication circuit, obtains a physical measurement from a user and communicates the physical measurement. The logic circuitry generates a predictive model that indicates a probability of the user having a hot flash at a date and time based on a plurality of input parameters, revises the probability based on the physical measurement using the predictive model, and communicates an instruction in response to the revised probability being outside a threshold. The cooling circuitry, which includes a communication circuit and heat transfer circuitry, provides cooling to the user in response to the instruction from the logic circuitry.

In various embodiments, the sensor circuitry includes a wearable physiological sensor to sense a physiological signal from the user and another sensor to sense an atmospheric measurement, and the cooling mitigates the hot flash for the user. In such embodiments, the sensor circuitry includes a plurality of sensors to obtain different physical measurements. Additionally, in some embodiments, the cooling circuitry includes a plurality of wearable cooling devices located at different physical locations of the user. The logic circuitry, in such embodiments, identifies which of the plurality of wearable cooling devices to communicate the instruction to and based on the predictive model.

In a specific and related embodiment, the sensor circuitry obtains and communicates additional physical measurements during the application of the cooling. The logic circuitry further revises the probability based on the additional physical measurements, and communicates another instruction in response to the further revised probability falling below the threshold. The revised probability falling below the threshold can indicate the hot flash is complete. In response to the other instruction, the cooling circuitry discontinues providing the cooling to the user.

Embodiments in accordance with the present disclosure include all combinations of the recited particular embodiments. Further embodiments and the full scope of applicability of the invention will become apparent from the detailed description provided hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWINGS

Various example embodiments may be more completely understood in consideration of the following detailed description in connection with the accompanying drawings, in which.

Figure 1:
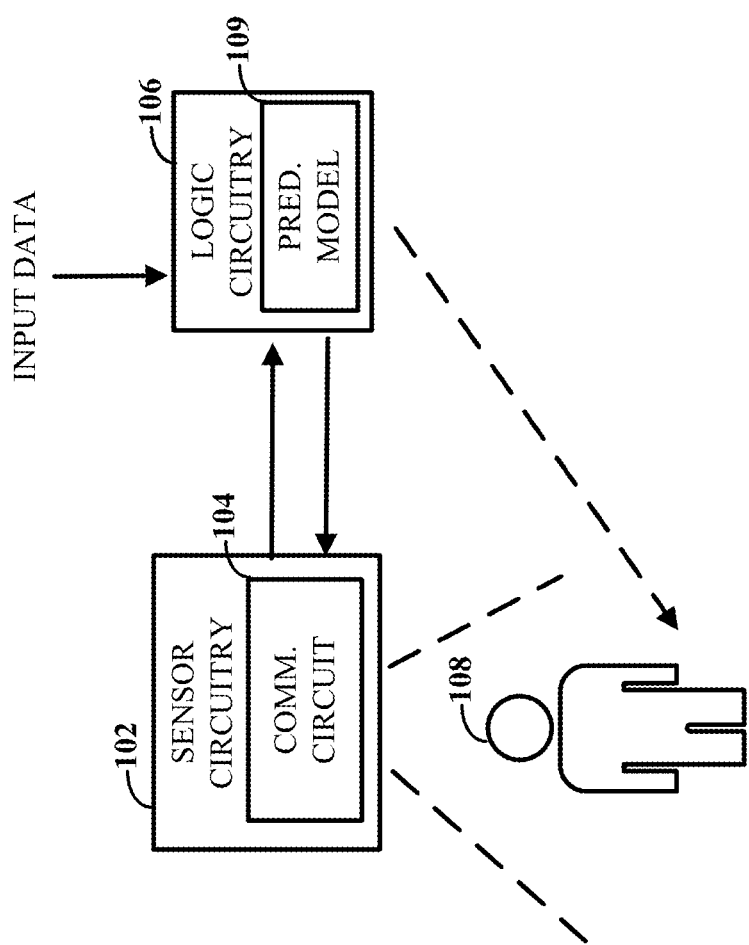
FIG. 1 illustrates an example of a system for hot flash management, in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of systems and methods involving a hot flash management system that can track hot flash occurrences over time, learn what biological, individual, and environmental factors may trigger hot flashes, and provides feedback to the user. In specific embodiments, the apparatus can provision cooling relief in advance of, or coincident with a suspected or imminent hot flash. While the present invention is not necessarily limited to such applications, various aspects of the invention may be appreciated through a discussion of various examples using this context.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Embodiments in accordance with the present disclosure involve a system for managing hot flashes. In specific embodiments, the system is a menopausal management system that aids in the management of menopausal symptoms. The system gathers data about a user and, based on the data, calculates the probability of a hot flash occurrence. The system may gather data about a user including data about when hot flashes occurred, analyze the data and present the results of the analysis. Additionally, the system may gather data about a user including data about which mitigation strategies worked best and present the results of that analysis to the user. Such a hot flash or menopausal symptom management tool can be linked with non-pharmacological therapies, such as cooling devices and/or stress relieving devices, which can provide sufficient relief from hot flashes in cases where pharmacological treatment is contra-indicated or not preferred. In related and specific embodiments, the system suggests mitigation techniques or triggers a mitigating action such as activating (e.g., turning) on a cooling device. These and other aspects are described below.

Various embodiments are directed to a system including sensor circuitry and logic circuitry, such as a hot flash management system and/or a menopause management system. The sensor circuitry obtains a physical measurement associated with a user and communicates the physical measurement. The physical measurement obtained by the sensor circuitry includes one or more of a physiological signal, an atmospheric measurement, motion data, and global position data. The sensor circuitry, in specific embodiments, includes a wearable physiological sensor to sense a physiological signal from the user. The sensor circuitry additionally or alternatively includes a sensor to sense an atmospheric measurement.

The logic circuitry generates a predictive model that indicates a probability of the user having a hot flash at a date and time based on a plurality of input parameters. Additionally, the logic circuitry revises the probability based on the physical measurement using the predictive model, and communicates data indicative of an action in response to the revised probability being outside a threshold. Revising a probability, in this regard, includes or refers to determining or generating a numerical value associated with the likelihood of an occurrence of a hot flash for the user using the predictive model and input parameters.

A variety of actions can be triggered by the logic circuitry. In some embodiments, the logic circuitry communicates data indicative of the action includes communicating a message to the user to take the action to mitigate a hot flash. In other embodiments and/or in addition, the data communicated may include an instruction to activate cooling circuitry. The cooling circuitry has a communication circuit and heat transfer circuitry to provide cooling to the user. In other embodiments and/or in addition, the logic circuitry provides an instruction to the sensor circuitry to adjust the physical measurement, as further described herein. Although embodiments are not limited to cooling actions, and may include other types of actions or interventions such as behavioral, environmental, and neurostimulation interventions.

The system, in accordance with various embodiments, is used to dynamically update the predictive model for a particular user over time based on additional input parameters and feedback data indicative of experienced (e.g., past) hot flashes. Such feedback data can include verification of an occurrence of a hot flash at a particular date and time, body location of the hot flash, and/or an indication of a severity or impact on the user. The feedback data can be input by the user and/or inferred using data obtained by the sensor circuitry. In specific embodiments, the severity or impact may be a scaled parameter, such as a user provided number of between 1-10, with 10 being the most severe or highest impact and 1 being the least impact. Other types of scales can be used. Based on the dynamic predictive model, the system is used to predict occurrence of a hot flash and to anticipate an imminent hot flash. As used herein, a predicted hot flash includes a hot flash that is suspected to occur at a particular time and date based on identified hot flash patterns of the user and the input parameters. The predicted hot flash is probability driven. An imminent hot flash is a hot flash that is about to occur (e.g., within one minute or thirty seconds). The imminent hot flash is identified based on a detected change in a physiological system (e.g., skin conductance change) of the user that is predictive of a hot flash about to occur. For an imminent hot flash, the system can proactively mitigate or prevent the hot flash using cooling or other actions. For a predicted hot flash, in some specific embodiments, the system can make suggestions to the user, proactively mitigate or prevent the hot flash, and/or increase the amount or sensitivity of physical measurement in order to more accurately detect an imminent hot flash and which can allow for reduced power consumption of the sensors (which can be in a lower power consumption mode prior to the predicted hot flash).

Turning now to the figures, FIG. 1 illustrates an example of a system for hot flash management, in accordance with various embodiments. The system 100 can be used for managing hot flashes and in specific embodiments, for managing menopause symptoms. However, embodiments are not limited to a menopause management system and can include a system used to manage hot flashes from other causes, such as prescription drugs or cancer treatment.

The system 100 includes sensor circuitry 102 and logic circuitry 106. The sensor circuitry 102 is used to obtain a physical measurement associated with a user 108. The sensor circuitry 102 has a communication circuit 104 for communicating the physical measurement to the logic circuitry 106. The communication circuit 104 can communicate in a wireless or wired manner.

The physical measurement may be a physiological signal or measurement (e.g., body fluids) from the user 108, motion, and/or an atmospheric measurement from the environment surrounding or near the user 108. For example, the sensor circuitry 102 may include a wearable physiological sensor, such as a wearable device, that senses the physiological signal from the user. The sensor circuitry 102 can alternatively or in addition include a sensor to sense an atmospheric measurement. Example physiological signals include parameters such as blood pressure, heart rate, skin conductance, body temperature, etc. Example atmospheric measurements include air temperature, atmospheric pressure, humidity, etc. Although embodiments are not limited to a physiological signal or atmospheric measurement and can additionally or alternatively include motion data (e.g., from accelerometer), and/or global positioning data (GPS).

The logic circuitry 106 generates a predictive model 109 indicative of a probability of the user 108 having a hot flash at a particular date and time based on a plurality of input parameters. Generating the predictive model 109 includes receiving input parameters and identification of past hot flashes for the user 108 or other users, identifying different patterns or correlation of occurred hot flashes and the input parameters, and, based on the patterns, identifying predictive probabilities of the user 108 having a hot flash at dates and times using additionally received input parameters. The input parameters include various categories of input data, including lifestyle and other hot flash factors for the particular user 108 and/or other users, as further described below, and the physical measurement(s) from the sensor circuitry 102. The logic circuitry 106 receives the plurality of input parameters, and uses the same to generate the predictive model 109. The parameters can be actively input by the user 108 or passively input or received. The input parameters include reported hot flashes, schedule or calendar data, lifestyle data including but not limited to stress level, mood, exercise data, sleep data, and dietary data, and health information including but not limited to physiological signals or parameters, medications, diagnosis, and other treatments, as well as various combinations thereof.

The predictive model 109 includes a probability that the user is having, is going to and/or is about to have a hot flash. In specific embodiments, the predictive model 109 includes a plurality of sub-models that each indicate the probability of the user having a hot flash at particular times of the day. Each of the sub-models is associated with a particular input parameter of the plurality parameters, which is sometimes herein referred to herein as a "category of input data", and has an associated weight. The weight may be based on or indicative of how predictive the respective input parameter is for the user to have a hot flash in the past or for other users to have a hot flash (e.g., how accurate of a predictor the parameter is for occurrence of a hot flash). The sub-models can include different patterns of occurrence of hot flashes for the user based on the particular input parameter. As previously described, the predictive model 109 can be used to predict hot flashes and to identify imminent hot flashes.

The logic circuitry 106 updates or revises this probability based on the physical measurement communicated from the sensor circuitry 102 using the predictive model 109. As a specific example, an increase in skin conductance, heart rate and/or a specific pattern of change in input parameters or signals (e.g., increased heart rate, increased skin conductance, and decreased blood pressure), along with other input parameters, may indicate the probability the user is having or about to have a hot flash is above a threshold. The threshold can be associated with a probable hot flash (e.g., the user is likely to have a hot flash), an imminent hot flash (e.g., the system anticipates the hot flash before it occurs), and/or a presently occurring hot flash.

The predictive model 109 can be dynamically updated over time. For example, the logic circuitry 106 revises the predictive model 109 over time using feedback data that is indicative of experienced hot flashes for the user and/or other users, and/or additional input parameters. Such feedback data can include verification of an occurrence of a hot flash at a particular date and time, body location of the hot flash, and/or an indication of a severity or impact on the user, and may be actively entered by the user to the system 100 and/or inferred from physical measurement received from the sensor circuitry 102. In specific examples, the feedback data is entered by the user and identifies changes in hot flash patterns over time. The update may include adjusting the weights of different input parameters based on the experienced hot flashes. As a specific example, over time, the user 108 may experience a change in hot flash occurrences that results in additional hot flashes at night and/or that are triggered by different parameters. In another example and/or in addition, the feedback may be indicative of specific information of the hot flash, such as a body location of the hot flash, severity or impact of the hot flash, and/or actions that are believed to result in mitigation of the hot flash. As may be appreciated, different users may experience relief, mitigation, and/or prevention of hot flashes using different actions. As a specific example, a particular user may have relief from hot flashes at different times of the day in response to cooling provided to different locations of the body.

In a number of specific embodiments, the predictive model 109 is dynamically updated over time based on the severity or impact of past hot flashes at particular times of the day and/or based on particular input parameters. The severity or impact may be a scaled parameter, such as a user provided number of between 1-10, with 10 being the most severe or highest impact and 1 being the least. Other types of numerical scales can be used, such as 0-100 or one to five stars. As specific examples, a hot flash at night that wakes up the user can have a higher impact than a hot flash that does not wake up the user. As another example, a hot flash while the user is in a meeting may have a higher impact than when the user is at home.

Based on the predictive model 109, which is dynamically updated over time, the system 100 is used to predict occurrence of a hot flash and to anticipate an imminent hot flash. For an imminent hot flash, the system can proactively mitigate or prevent the hot flash using cooling or other actions. For a predicted hot flash, in some specific embodiments, the system 100 makes suggestions to the user, proactively mitigates or prevents the hot flash, and/or increases the amount or sensitivity of physical measurements in order to more accurately detect an imminent hot flash and which can allow for reduced power consumption of the sensor circuitry 102 (which can be in a lower power consumption mode prior to the predicted hot flash).

The logic circuitry 106 may communicate data indicative of an action in response to the revised probability being outside, such as above, the threshold. The action may include communicating a message to the user 108 to take an action to mitigate or prevent the hot flash and/or to otherwise mitigate symptoms associated with the hot flash and/or menopause. The action may be based on past user response to an action by the system 100 and/or other users' response to mitigating action to prevent or mitigate hot flashes and/or other symptoms. In other embodiments and/or in addition, the action includes a computer-readable instruction that is communicated to another device, such as to the sensor circuitry 102, to cooling circuitry, or other devices such as temperature control circuitry (e.g., associated with a heating, ventilation, and air conditioning (HVAC) system). As non-limiting examples, the action can be an instruction provided to an HVAC system to change the temperature of a particular room, an instruction to a user device to provide a notification to the user, such as a smart watch beeping to notify the user of a likely or imminent hot flash, and/or a display on an application executed by a smartphone which instructs the user on a particular action to take, among other specific actions. As another specific example, and further illustrated by FIG. 2, the action can include an instruction to activate cooling circuitry to provide cooling to the user in response to the instruction. In various embodiments, an action may include an instruction communicated back to the sensor circuitry 102, which causes the sensor circuitry 102 to adjust the physical measurement (e.g., increase or decrease the sensitivity and/or number of measurements). As may be appreciated, embodiments are not limited to a single action and multiple actions may be triggered by the system 100. Other example actions may include suggestions to the user or actions for stress relief, which may mitigate the hot flash occurrence(s) or severity. Example stress relief strategies may include cognitive behavior therapy, music therapy (e.g., activate a device to play music to the user or recommend the same to the user), and/or aromatherapy (e.g., active a device outputs a scent or recommend the same to the user, such as lavender, chamomile, or rose scents). Example suggestion may include recommending the user exercise, take supplements, aromatherapy, play music, reduce caffeine intake, chewing gum, deep breathing exercises, among other recommendations.

In specific embodiments, the revised probability being outside the threshold indicates that a hot flash is imminent for the user, e.g., to occur within 30 seconds. In other embodiments, the revised probability being outside the threshold indicates that the hot flash is occurring or is predicted to occur at the date and time. In various embodiments, the logic circuitry 106 utilizes multiple thresholds, which may cause different actions to occur in response to the probability being outside a respective threshold of the multiple thresholds. As a specific and non-limiting example, the logic circuitry 106 provides an instruction to the sensor circuitry 102 to adjust the physical measurement in response to the probability being outside a first threshold and within a second threshold, with the first threshold being associated with a predicted hot flash and the second threshold be associated with an imminent hot flash. The adjustment may include an increase in sensitivity or number of measurements made by the sensor circuitry 102. The logic circuitry 106 additionally provides a message to the user or an instruction to the cooling circuitry in response to the probability being outside the second threshold, with the second threshold being associated a higher probability than the first threshold. In such a manner, the logic circuitry 106 can cause the sensor circuitry 102 to take more measurements and/or increase sensitivity in response to predicting a hot flash is likely, and which may reduce power consumption of the sensor circuitry 102 at times when a hot flash is predicted to be unlikely (e.g., the probability is below the other threshold). In other embodiments and/or in addition, the logic circuitry 106 provides an instruction to the sensor circuitry 102 to decrease the sensitivity and/or number of measurements/timing of measurements in response to the probability being below the first (and/or a third) threshold.

In specific embodiments, the system 100 includes a menopause management system used in management of a plurality of menopausal symptoms, including hot flashes. The menopause management system can additionally manage, e.g., mitigate or prevent, symptoms such as chills, night sweats, sleep problems, and mood swings and/or general poor mood.

Figure 2:
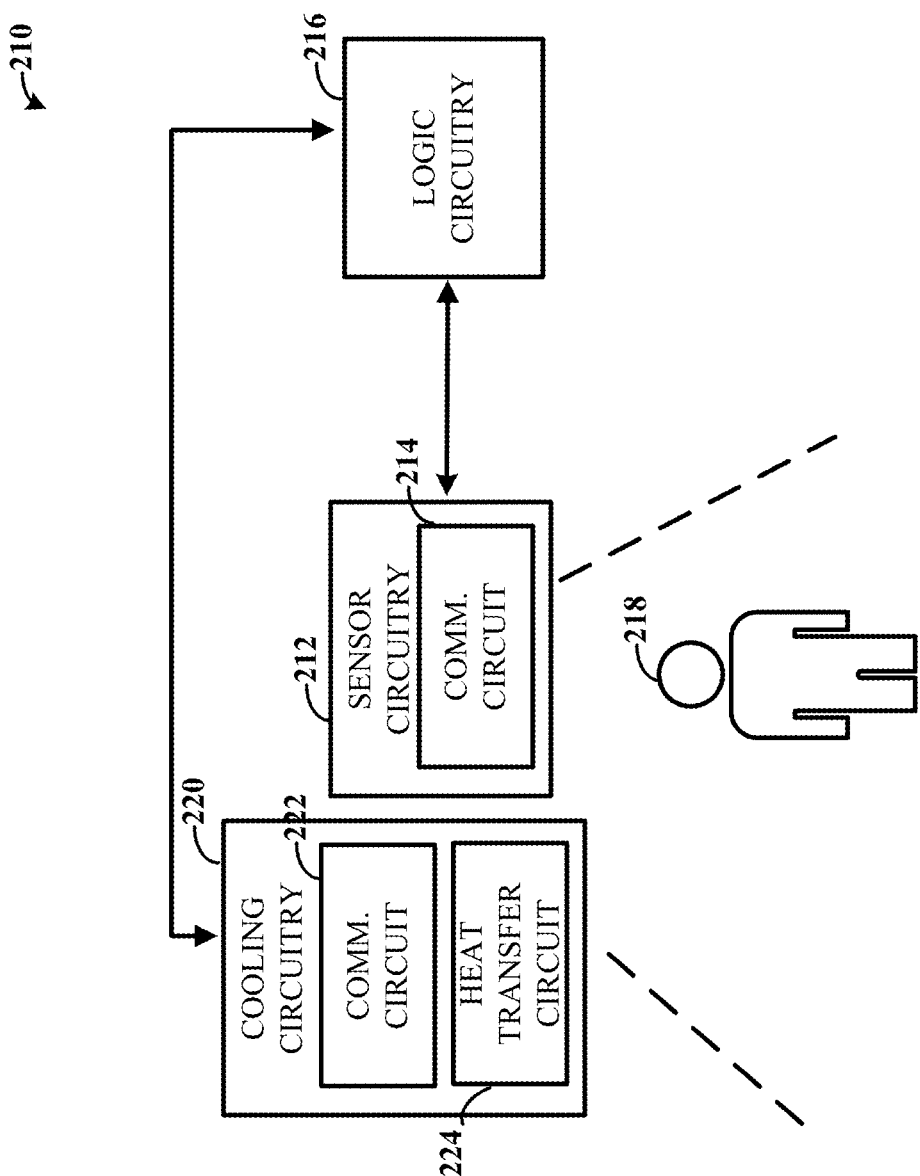
FIG. 2 illustrates another example system for hot flash management, in accordance with various embodiments.

FIG. 2 illustrates another example system for hot flash management, in accordance with various embodiments. The system 210 includes logic circuitry 216 and sensor circuitry 212 having a communication circuit 214, as previously described in connection with FIG. 1, and additionally includes cooling circuitry 220.

Similarly to that described in connection with FIG. 1, the sensor circuitry 212 obtains a physical measurement from the user 218 and communicates the physical measurement using the communication circuit 214. Although the sensor circuitry 212 is illustrated as a single sensor, embodiments are not so limited. For example, the sensor circuitry 212 can include a plurality of sensors that obtain different physical measurements, such as different physiological signals, atmospheric measurements, motion data, and/or GPS signals. In a specific embodiment, the sensor circuitry 212 includes a wearable physiological sensor to sense a physiological signal from the user and another sensor to sense an atmospheric measurement, as previously described.

The logic circuitry 216 generates a predictive model that indicates the probability of the user 218 having a hot flash at a date and time based on a plurality of input parameters. The logic circuitry 216 revises the probability based on the physical measurement using the predictive model and communicates an instruction to the cooling circuitry 220 in response to the revised probability being outside a threshold.

The cooling circuitry 220 includes communication circuity 222 and heat transfer circuitry 224. The cooling circuitry 220 responds to the instruction by providing cooling to the user 218 using the heat transfer circuitry 224. Example heat transfer circuitry 224 includes a fan, an air-conditioning/refrigerant based circuit, thermal cooling circuitry, heat sink circuitry, etc. The instruction actives the cooling circuitry 220 and, in response, cooling is provided to the user 218 to mitigate and/or prevent an occurrence of a hot flash. Although the cooling circuitry 220 of FIG. 2 is illustrated as a single circuit, embodiments are not so limited and the cooling circuitry 220 can include a plurality of wearable cooling devices that are located at different physical locations of the user 218 in some specific embodiments, such as for a particular user that experiences hot flashes at what is perceived by the user to be different locations of their body. In such embodiments, the logic circuitry 216 identifies which the plurality of wearable cooling devices to communicate the instruction to and based on the predictive model. The cooling devices can be located at different physical locations to either actively remove heat to cool the body and/or to provide a sensation of cooling to the user. Additionally, the cooling devices can be located to cover variable surface areas of the body, from small areas with localized cooling to large areas, such as the whole back for variable amounts of heat loss.

The logic circuitry 216 may further deactivate the cooling circuitry 220, thereby stopping the cooling. The deactivation may be based on the predictive model which identifies a specific amount of cooling time and/or additional measurements by the sensor circuitry 212. For example, the sensor circuitry 212 obtains and communicates additional physical measurements during the application of cooling. The logic circuitry 216, in such embodiments, further revises the probability based on the additional physical measurements and communicates another instruction to the cooling circuitry 220 in response to the further revised probability falling below the threshold (or a different threshold), which indicates that the hot flash is complete or near complete. The cooling circuitry 220, in response to the other instruction, discontinuous providing the cooling to the user 218.

Figure 3:
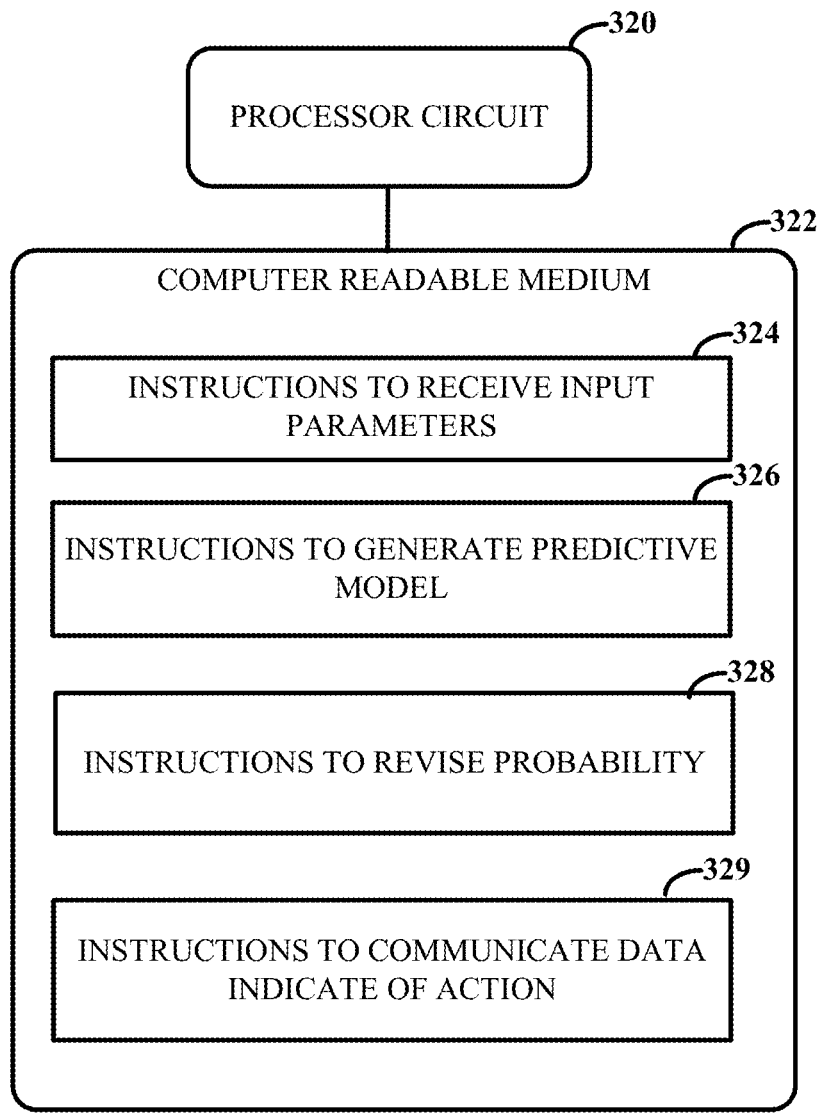
FIG. 3 illustrates an example computing device including non-transitory computer-readable medium storing executable code, in accordance with the present disclosure.

FIG. 3 illustrates an example computing device including non-transitory computer-readable medium storing executable code, in accordance with the present disclosure. The computing device, in accordance with examples herein, includes a user device having logic circuitry, such as the logic circuitry illustrated by FIGS. 1-2.

The computing device has a processor circuit 320 and computer readable medium 322 storing a set of instructions 324, 326, 328, 329. The computer readable medium 322 may, for example, include read-only memory (ROM), random-access memory (RAM), electrically erasable programmable read-only memory (EEPROM), Flash memory, a solid state drive, and/or discrete data register sets. At 324, the computing device may receive a plurality of input parameters indicative of hot flash factors for a user and a plurality of users. At 326, the computing device generates the predictive model to indicate a probability of the user having a hot flash at a date and time based on the plurality of input parameters. At 328, the computing device revises the probability using the predictive model and based on a physical measurement obtained from the user, which is received from sensor circuitry. At 329, the computing device communicates data indicative of an action in response to the revised probability being outside a threshold, the action being based on user response to the action. For example, the action may be based on past responses of the user to the action or other users to the action, and that include mitigation and/or prevention of a hot flash and/or other menopause symptoms.

In various embodiments, the communicated data includes an instruction that activates cooling circuitry worn by the user. In response to the activation, the cooling circuitry provides cooling to the user to mitigate or prevent an imminent or occurring hot flash. The computing device may further generate another instruction to deactivate the cooling circuitry, in response to a further revised probability based on an additionally received physical measurement being within the threshold. Similarly to that described above, the computing device may further provide an instruction to the sensor circuitry to adjust the physical measurement in the response to the probability being outside another threshold and within the threshold, which indicates a predicted but not imminent hot flash. The predictive model may be revised over time based on additional input parameters. For example, the user may provide feedback data indicative of the user response to the action, and which may be used to revise the action and/or parameter weights.

Figure 4:
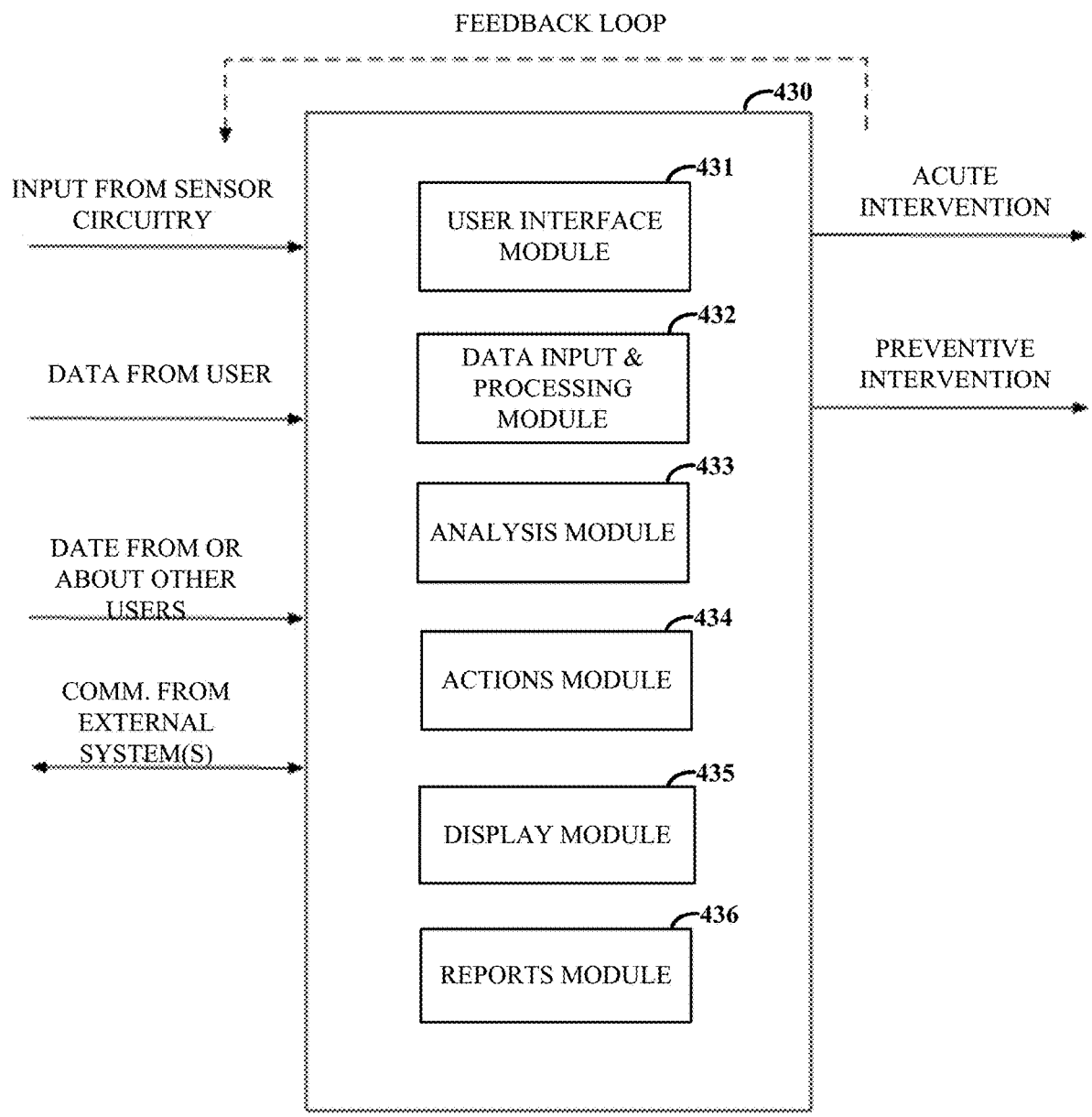
FIG. 4 illustrates an example menopause management system, in accordance with various embodiments.

FIG. 4 illustrates an example menopause management system, in accordance with various embodiments. The menopause management system 430 quantifies the contribution of hot flashes to the amount of wakefulness during the night, in specific embodiments and as further illustrated by the index of FIG. 12. The menopause management system 430 can include a program implemented on a computer device that is able to predict occurrence of hot flashes based upon information previously entered.

The management system 430 may be configured in multiple ways. Some embodiments of the menopause management system 430 can be or form part of a computer program or application that can run on a smartphone, a tablet, a desk computer, a laptop, smart watch, exercise tracker, or other independent device. In other embodiments of the menopause management system can be a web-based program. In any of the above embodiments, the program can include the executable code such as illustrated by FIG. 3.

In general, a user of the menopause management system is a single "subject". In other configurations of the menopause management system, one system can be used by multiple subjects for monitoring and storing each person's personal hot flash episode.

More specifically, FIG. 4 illustrates a functional block diagram of a menopausal management system 430 that aids women in the management of their menopausal symptoms. In the specific embodiment shown in FIG. 4, the menopause management system 430 includes a user interface module 431, a data input and processing module 432, an analysis module 433, an actions module 434, a display module 435, and a reports module 436. Although embodiments are not so limited and the menopausal management system 430 may include fewer or more modules than illustrated by FIG. 4. Each of the modules 431, 432, 433, 434, 435, 436 includes computer executable code which may be stored on one or a plurality of non-transitory computer-readable medium and executed by one or more processor circuits, such a single computing device or distribution across multiple computing devices.

The user interface module 431 is the portion of the menopause management system 430 that allows a user to interface with the other modules integrated into and/or that form part of the menopause management system 430. The user interface module 431 can be utilized to accept input data from the user. Data can be accepted by other modules as well. In some embodiments, the user can actively and/or passively input information into the menopause management system 430 in a variety of ways. A user may choose to manually enter data. A user can verbally enter information into the menopause management system. A user can upload health-related files to the menopause management system 430. In other embodiments, the user can grant the menopause management system 430 access to data on other applications and/or other external locations, such as calendar data, exercise or food tracking applications.

Using the user interface module 431, the user may enter personal data via input hardware (e.g., a mouse, a keyboard, a touch screen, a microphone etc.) such as but not limited to demographics, body mass index (BMI), ethnicity, age, menopausal status, medications, mood during a particular time of the day, anxiety level, activity level, allergies, types of food ingested, etc. The user interface module 431 can also be used to self-report hot flashes. The self-report can be compared with any sensed values and the results can be used to predict onset of future hot flashes or the information can be presented to the user. In general, the user interface module 431 can be used to obtain data from the user. The system 430 can elicit responses or prompt the user to perform a certain action by displaying a message and requesting a response that is entered through the user interface. The responses need not be typed—the system 430 can include a speech processing module to interpret speech and parse out the responses.

The data input and processing module 432 is the portion of the menopause management system 430 that stores data provided by the user through the user interface module 431 or "pre-packaged" data that can be loaded onto the menopause management system 430 to be used in conjunction with data collected from the one or more sensors in communication with the data input and processing module 432. The data input and processing module 432 may also accept data from other modules that can be part of or independent of system 430.

The data input and processing module 432 can also process data from the sensors. Processing can include, but is not limited to low pass filtering, noise reduction, feature extraction, and so forth. Extracted features are temporal and/or spectral features representing the data and its specific time pattern, variabilities and frequency content. Temporal features can include statistical measures such as mean, variance, and higher order statistics of the input data in a time frame. Spectral features can be extracted using Fourier transform. Spectral features in one example can be spectral moments, spectral power fractions, spectral power peaks, and spectral power ratios. The features can also be extracted after applying an appropriate transform that facilitate the understanding of the input pattern such as wavelet transform. Features can also include parameters of a model best representing the data in a specific time window.

Because the dimension of the input patterns may be very high, statistical methods such as principal component analysis or linear component analysis are used to transform the features into a lower dimension subspace where a more precise and efficient representation of the input patterns can be achieved. An effective data representation of input data can improve the learning and generalization capability of the system 430, while redundant input data, may decrease the discrimination capability of the system 430 and lead to degradation in the learning process. Several analytical techniques (e.g., Granger causality, transfer entropy) can be used to derive information from the dynamic relationships between multiple physiological inputs and use those computational outputs as input variables for the system 430.

The analysis module 433 is the portion of the menopause management system 430 that accepts data from the data input and processing module 432 and performs various types of analyses including but not limited to generating predictive model and analyzing the impact of hot flashes on sleep, cardiac function, mood and daytime activities. The analysis module 433 analyzes the impact of factors implicated in the severity and manifestation of hot flashes, including but not limited to environmental circumstances (e.g., ambient temperature, humidity, season, time of day, meal composition, caffeine and/or alcohol consumption, use of medications), individual circumstances (e.g., mood, stress, anxiety, time of day, exercise, menstrual cycle patterns, calendar events), users' location from GPS and/or user inputs (e.g., supermarket, home, work), and physiological state (e.g., skin temperature, thermosensitivity, heart rate, cardiac autonomic state, such as heart rate variability, skin blood flow, such as peripheral vasoconstriction/vasodilation) to assess the severity and manifestation of hot flashes. In some specific embodiments, the physiological state of the user is based on hormone levels, such as input data from a physician, the user, or a biosensor. As a more specific example, a biosensor provides information on hormone levels (e.g., estradiol), such as from interstitial fluid or sweat of the user, or other substance present in the bodily fluids, such as alcohol or other substance in sweat or interstitial fluid.

The actions module 434, for example, accepts the output of the analysis module 433 and takes or suggests interventions. In general, there are two general types of interventions conceived for the menopause management system—acute intervention and preventive intervention. An example of acute intervention includes but is not limited to providing spot cooling to one or more locations on a subject's body or turning on a fan or other cooling device in close proximity to the subject. This is described in more detail below. An example of preventive intervention includes but is not limited to suggesting activities (e.g., slow breathing, physical exercise) and/or behaviors (e.g., changing in nutrition plan, weight management) that has, e.g., in the past, reduced the incidence of hot flashes for a particular subject (e.g., based upon a particular subject's physiological and lifestyle profile). Other example preventative interventions include an acute intervention. A specific example actions module 434 is further illustrated by FIG. 8.

In specific embodiments, the action(s) may be aimed at modulating sleep macrostructure, such as sleep stage composition. Such actions may include cognitive behavior therapy and sleep neurostimulation (e.g., acoustic stimulating during the night). Such actions may improve the deep sleep state of the user, thereby decreasing a probability the user will wake up in the night during a hot flash occurrence and potentially reducing stress levels. The actions may be based on or include virtual reality (VR) techniques and methodologies to reduce stress/arousal more effectively before sleep and, as a result, improve a deep sleep state of the user. VR may, for example, be used for mitigating or reducing pre-sleep stress level or reducing stress levels at any time across the day with the assumption that less stress may result in less number and/or severity of hot flashes (e.g., following the rationale that autonomic nervous system is implicated in the pathophysiology of hot flashes, and not only thermoregulation). VR may be used as a tool and in addition to other strategyies to reduce stress (e.g., meditation, biofeedback, slow breathing, visual imagery, etc), with some of these strategies being indicted in the pre-sleep period and some more during the day.

Apart from the user entered data, the system 430 may also accept data from other sources including but not limited to physiologic sensors, environmental sensors, data entered into other applications that are run on the same platform etc. With regard to physiologic sensors, the sensors may include but are not limited to skin conductance sensors, skin temperature sensors, blood pressure sensors, pulse rate sensors, photoplethysmogram sensors, electrocardiogram sensors, and electroencephalogram sensors. Various physical forms of the sensors may be utilized such as but not limited to sensors that are adhesively coupled to the body, sensors that are housed in wearables and sensors that are coupled or attached to clothing.

With regard to environmental sensors, the system may accept data from external sensors that are capable of communicating with the system or it may accept data from sensors already integrated within the system. With an example system that exists in the form of a mobile application, the sensors that already exist within the mobile device may be utilized to provide the input data into the system. Environmental data may include time of day, local temperature, local humidity, light exposure etc. Some of this data may be measured locally if sensors are utilized but in some cases, the data may be obtained from another application or an external source, such as from a website. In this case, the system may initiate a search automatically to obtain such data for the location of the user. This type of data input may be conveniently acquired if the system existed in the form of a mobile application. With regard to obtaining data from other applications, such data includes, but is not limited to, meeting data from calendar applications, or data from other menstrual management applications that may be obtained by interacting with one or multiple of these applications.

Yet another form of data is in the form of inferred data. An example of this is the use of an emotional detection module to detect emotion of the subject. The emotion detection module can interact with the data input and processing module 432 and send the results of the analysis. As described above, emotional state data can be collected through user input of their mood or may be assessed based on a combination of physiological parameters that are detected or entered As previously described, the data input and processing module 432 can also process the data to make it more suitable for analysis. Data from each source can be processed differently. For example, processing of data from physiologic sensors includes but is not be limited to low pass filtering, averaging, smoothing, and so on. Microphone data for emotionality analysis can be also similarly filtered to remove any spurious sounds. Data from websites can also be used directly. Also, sensors that produce complex waveforms such as electrocardiogram (ECG) or electroencephalogram (EEG) sensors, can be depicted by extracted parameters. For ECG, the data input and processing module 432 can extract a number of parameters such as pulse rate (PR) interval, duration of QRS complex, R-R interval etc., and store this information along with the date and time of the measured parameters.

The analysis module 433 can be executed to provide a number of functions including providing a real-time probability of occurrence of a hot flash, whether imminent or at some future time, and analyzing what conditions are most likely to trigger hot flashes for each user (based on analysis of data gathered by the system), which is sometimes herein referred to as the "predictive model". In addition, the analysis module 433 can be executed to analyze the data obtained after mitigating measures are taken and report on which mitigating measure is the most effective for that person, and which may be based on feedback data.

The calculation of the probability of occurrence, e.g., the predictive model, is further described below. With regard to the analysis of triggers, the analysis module 433 can analyze all data that is available to it along with the data of hot flash occurrence and determine the conditions that are most likely to cause hot flashes for the particular subject, which are sometimes herein also referred to as "hot flash factors". An example method is described below.

TABLE 1

| Hot flash occurrence | | | |
|---|---|---|---|
| Condition 1 | Condition 2 | Condition 3 | Occurrence |
| Present | Not Present | Present | Hot flash occurred |
| Present | Not Present | Not Present | Hot flash occurred |
| Not present | Not present | Present | Did not occur |

The system 430 can generate a table such as Table 1, with the conditions that occurred when each hot flash occurred, or did not occur, being noted. The conditions can be the inputs that the system 430 gathers. While Table 1 shows three conditions, the number of columns are not so limited and can encompass any number of inputs. Other non-limiting examples of user conditions may be skin conductance, humidity, time of day, location, meeting with a particular person, stress level, and so on. For inputs that are in the form of waveforms such as EEG and ECG, one or multiple parameters can be extracted such as in the example of an ECG, the R-R interval etc. In the simplified example in Table 1, by examining the conditions that are prevalent when hot flashes occur, one hypothesis that may be reached is that condition 1 has a high likelihood of triggering a hot flash. Thus this hypothesis may be displayed or conveyed to the user.

The above concept can be extended to also generate a hypothesis of which mitigating actions are more effective. A table such as Table 2 may be generated:

TABLE 2

| Condition 1 | Condition 2 | Condition 3 | Mitigating action 1 | Mitigating action 2 | Mitigating action 3 | Occurrence |
|---|---|---|---|---|---|---|
| Present | Not Present | Present | | | | Hot flash occurred |
| Present | Not Present | Not Present | | | | Hot flash occurred |
| Not present | Not present | Present | | | | Did not occur |
| Present | Not present | Not present | Present | Not present | Not present | Did not occur |
| Present | Not present | Not present | Not Present | Present | Not present | Hot flash occurred |

In Table 2, along with the conditions, the table includes collected information about which mitigating action provided relief. In this example, for condition 1, mitigating action 1 seems to be effective, while mitigating action 2 did not appear effective in mitigating a hot flash. This hypothesis may be conveyed to the user. The data collected for a particular user can include identification of mitigating actions applied after a particular condition is detected and whether that mitigating action was effective in preventing a hot flash, which can better enable the system 430 to predict and mitigate future hot flashes.

The above analysis may be done with an analysis module 433 used for performing computations and/or with a machine learning (ML) processes. In specific embodiments, the analysis module 433 can be or include a predictive engine. An engine includes a special-purpose program which uses deep learning to query data.

The display module 435 allows a user to interact with the menopause management system 430. The display module 435 may provide the user with visual representation of the probability (e.g. how likely a hot flash may occur). The display module 435 may be used as an interface where the user can input or otherwise communicate information (such as mood, food and beverage type and quantity, and so forth) to the data input and processing module 432 so that the analysis module 433 can better predict occurrence of a hot flash based on this additional input data.

In some embodiments, the menopause management system 430 can include a reports module 436. The reports module 436 is used to generate summaries of hot flash occurrences for a user and/or for each of a plurality of users. Summaries can include information regarding when the hot flashes occurred, the circumstances under which the hot flashes occurred, what type of mitigation was attempted, whether the hot flash mitigation event was successful or not, and so forth. In some embodiments, the user is able to customize the summary, where the customized summaries can include information that the user pre-selects, how often the summaries are generated for the user, and so forth. In some instances, the reports module 436 can also pull updated health data for a particular user from the user's healthcare provider or the user's healthcare provider can provide updated health information to the menopause management system 430.

In more specific embodiments, the reports module 436 is used to create a report that summarizes each action or tip that the actions module 434 generates or recommends and a degree of success experienced (e.g., regarding prevention or mitigation of hot flash or other system reduction). The report can be provided along with identified data and other information to an appropriate external computing system or resource (e.g., a health care provider). The other information may include various information that is either sensed, entered, inferred or found such as but not limited to the diet of the subject, the physical activities the subject engages in, etc.

In various embodiments, the menopause management system 430 can include or form part of a computer program or application that can run on a smartphone, a tablet, a desk computer, a laptop, smart watch, exercise tracker, or other independent device where the computer program or application that can run on a smartphone, a tablet, a desk computer, a laptop, smart watch, exercise tracker, or other independent device that can be contained within a wearable device or which is in data communication with a wearable device.

In some embodiments, the menopause management system 430 can include or be in communication with a wearable smart garment. The wearable smart garment is in communication with the menopause management system 430 through a smart device, computer, or so forth. Such menopause management wearable garments may be worn underneath a user's normal clothing. In some embodiments, the menopause management wearable garment may include temperature and moisture sensors to help predict the onset of hot flashes. The monitoring garments may include sensors that detect other physiological parameters in addition to respiration and heart beat and rhythms. For example, such monitoring garments may include sensors for detecting a wearer's body temperature, heart rate, moisture level, and so forth, where these physiological values are then recorded within the menopause management system 430 to better predict hot flash occurrences. In other and/or related embodiments, the menopause management system 430 may include circuitry that provides a mitigating output in response to predicted hot flash onset based upon sensor readings/settings. Non-limiting examples of the menopause management wearable garment form may be a bra, an undershirt, a garment that wraps around the user's midsection, and so forth.

In some embodiments, the menopause management system 430 may be coupled to one or more menopause management devices, which may include cooling circuitry as previously described. In some embodiments, the menopause management devices can be integrated with the menopause management system 430 into one application or device that a user can use to mitigate the effects of hot flashes. One non-limiting example is a wearable bracelet or watch-type device that includes the menopause management system, where the bracelet or watch is able to provide a mitigating output in anticipation of a hot flash based upon a predicted onset of hot flash from the subject's biological data. Some examples of outputs for mitigating hot flashes are cooling to the corresponding area where the device is positioned, possible application of pressure to certain pressure point, and so forth.

In some embodiments, the menopause management system 430 is able to communicate with other external devices that are then able to provide relief for hot flash symptoms. Non-limiting examples of such external devices that are in data communication with the menopause management system 430 can be a fan, smart blanket, sleeping pad, temperature control for a room, and so forth, where the menopause management system 430 provides at least one output based upon predicted occurrence of a hot flash for relieving or mitigating the effects of the hot flash. In some embodiments, the external devices may be in either wired or wireless communication with the device on which the menopause management system 430 is running.

Figure 5:
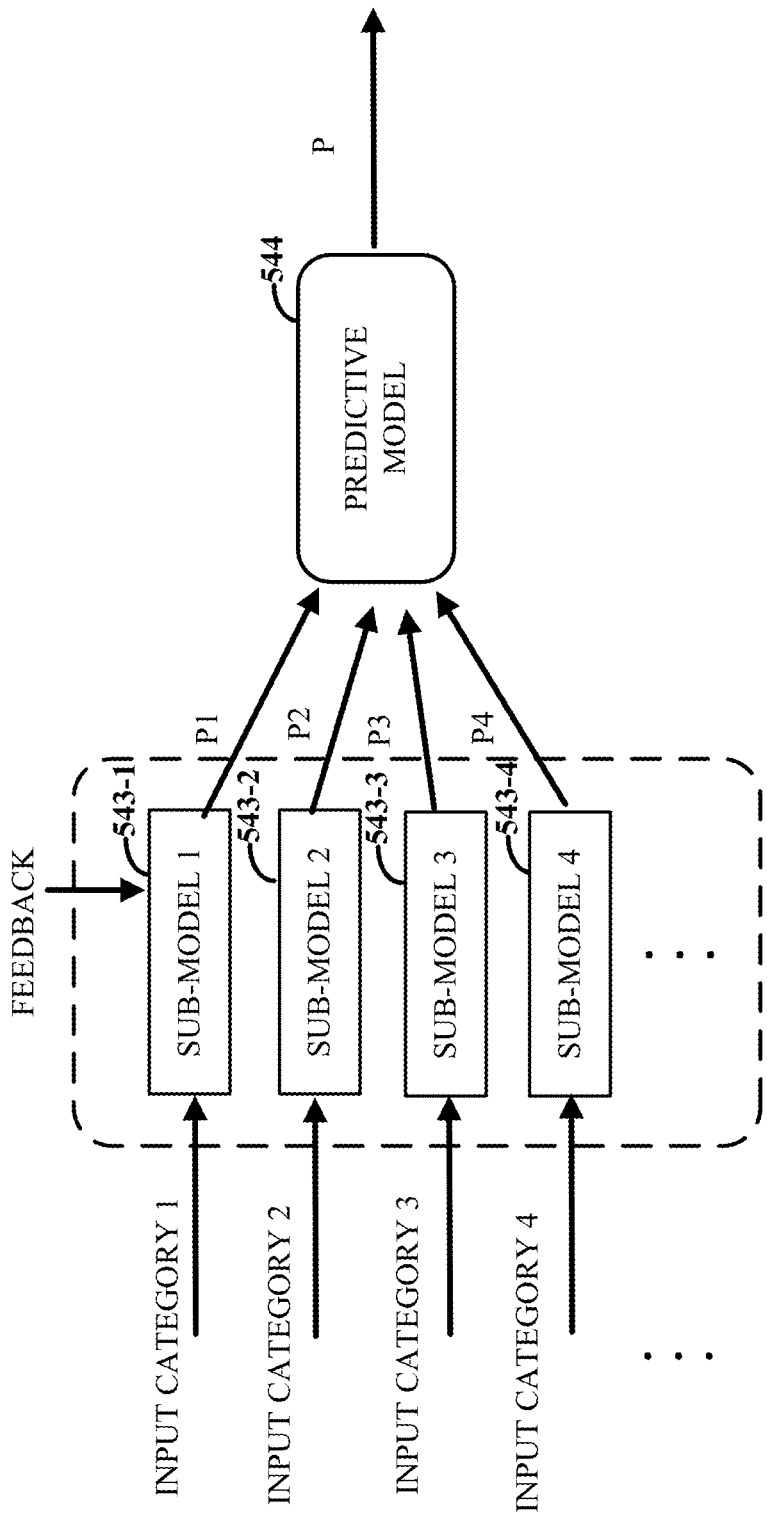
FIG. 5 illustrates an example process for generating a predictive model, in accordance with various embodiments.

FIG. 5 illustrates an example process for generating a predictive model, in accordance with various embodiments. As described above, the analysis module 433 illustrated by FIG. 4 may be executed to generate a predictive model 544 that indicates a probability of the user having a hot flash at a particular date and time based on a plurality of input parameters (e.g., input data).

The predictive model 544, sometimes referred to as a probability engine, accepts several different input categories including 1) physiological signals collected with non-invasive sensors and systems, 2) user's routine including data extracted from the user's calendar, GPS location, etc., 3) environmental sensors including temperature, humidity, and so forth, and 4) user's self-report or input into the system, such as mood, energy level or physical state, food or drink intake over the course of the day, medication, supplements, and so forth. The predictive model 544 can also be informed by scientific discoveries in the literature, such as health web-sites, online feeds, and/or journal articles, that can serve as an additional input. The output of the predictive model 544 is the current and/or future probability of a hot flash occurring (e.g., depending of the actions module parameters set for triggering such as real-time cooling, which uses the current hot flashes probability or tips and the future hot flashes probability to take preventive action). A non-limiting example is where the actions module, as previously described, can be programed to initiate cooling if a user's body temperature rises above 99.5° F. and where the relative humidity is above 75% at air temperature of 80.0° F. Another non-limiting example includes where the actions module can be programmed to initiate cooling when the user indicates that she is feeling stressed and her heart rate increases to above a threshold level that is tailored for each user (e.g., 100 beats per minute).

The inputs are processed according to their categories and type to obtain a representation that allows the analysis module to learn their pattern with respect to the hot flash occurrence for a particular person, and which may include use of different machine learning processes to generate sub-models. A generalized machine learning process is further illustrated in FIG. 6. Different machine learning (ML) processes are incorporated in the predictive model 544 depending on the input categories. Each machine learning process is used to build a sub-model 543-1, 543-2, 543-3, 543-4 between the inputs and the outputs which are current and/or future probabilities of hot flash occurrence. Based on the "gold standard" measure of hot flashes (e.g., skin conductance signal) and user self-report inputs about hot flash occurrence and severity, the parameters of the predictive model 544 are optimized by minimizing a cost function of each of the sub-models 543-1, 543-2, 543-3, 543-4. The cost function is a function that maps the model predicted probability onto a real number intuitively representing some "cost" associated with the predicted probability value.

The following provides example input data. The examples are not intended to be limiting and additional or fewer categories can be used.

As shown in FIG. 5, an example first input data category for sub-model 1 543-1 can include raw physiological signals or extracted features of them. Extracted features are temporal and/or spectral features representing the physiological signals and their specific time pattern, variabilities and frequency content. Temporal features can include statistical measures such as mean, variance, and higher order statistics of the input data in a time frame. Spectral features can be extracted using Fourier transform. Spectral features in one example may be spectral moments, spectral power fractions, spectral power peaks, and spectral power ratios. The features can also be extracted after applying an appropriate transform that facilitates the understanding of the input pattern such as wavelet transform. Features could also include parameters of a model best representing the data in a specific time window. Since the dimension of the input patterns is very high, statistical methods such as principal component analysis or linear component analysis may be used to transform the features into a lower dimension subspace where a more precise and efficient representation of the input patterns is achieved.

A second input category for sub-model 2 543-2 may include calendar data. To learn from the calendar, the time and the type of the events are extracted and used to form a chart of time events as follows:

TABLE 3

Organizing calendar events

| | Time1 | Time2 | Time3 | Time4 | Time5 | Time6 | Time7 | ... | Timem |
|---|---|---|---|---|---|---|---|---|---|
| Event 1 | 0 | 0 | 0 | 0 | 0 | 0 | 0 | ... | 1 |
| Event 2 | 1 | 0 | 0 | 1 | 0 | 0 | 0 | | 0 |
| Event 3 | 0 | 0 | 0 | | 0 | 0 | 1 | | 0 |
| Event 4 | 0 | 0 | 0 | | 0 | 0 | | | 0 |
| ... | | | | | | | | | |
| Event n | 0 | 0 | 0 | 1 | 0 | 0 | 0 | | 0 |

In the matrix (chart) of the time/events the occurrence of an event at a specific time interval is marked by 1 and the rest of the elements are marked by 0s. Assuming there are n events and m time intervals, the matrix forms an array of m by n dimension. These form the inputs to the sub-model 2 543-2 that outputs the probability $P_i$ of the hot flash occurrence over any specific time frame i. Assuming there is m time intervals, the output of the sub-model 2 543-2 can be presented as follows:

TABLE 4

| | Time1 | Time2 | Time3 | Time4 | Time5 | Time6 | Time7 | ... | Timem |
|---|---|---|---|---|---|---|---|---|---|
| Outputs | $p_1$ | $p_2$ | $p_3$ | $p_4$ | $p_5$ | $p_6$ | $p_7$ | | $p_m$ |

In this example, not only the relationship between a specific event and the occurrence of a hot flash is modeled, but also any relationship between the occurrence of a hot flash and a pattern of different events in time may be extracted. This inputs can be directly fed to the predictive model 544 or features can be extracted from the inputs. Statistical methods such as principal component analysis can be used for feature extraction and dimensionality reduction of the calendar inputs.

The sub-model 2 543-2 takes inputs related to the user's routines during a specific time such as twenty-four hours, and outputs the probability of hot flash occurrences during that time. Therefore, the output of the machine learning process consists of m hot flash occurrence probabilities corresponding to m time intervals. Machine learning methods such as multiple regression, genetic programming, support vector regression, and difference structures of neural networks can be used for this purpose. As an example, a multi-layer perceptron (MLP) neural network with m outputs can be trained for this purpose. The basic structure of the network may be the system shown in FIG. 10, in some specific embodiments. However, the output layer may consist of m nodes with logistic activation functions so that each output would be between 0 and 1. The cost function to be minimized here could be the mean squared error and the optimization algorithm can be set to backpropagation.

The different events in the calendar may be extracted using natural language processing (NLP) techniques and are classified or clustered into several group according to their similarity. In an example, different events can be classified into predefined classes using algorithms such as centroid categorization, naive Bayes, etc. In another example, the events may be clustered using partitioning algorithms such as K-Means or hierarchical algorithms including agglomerative and divisive approaches.

Figure 7:
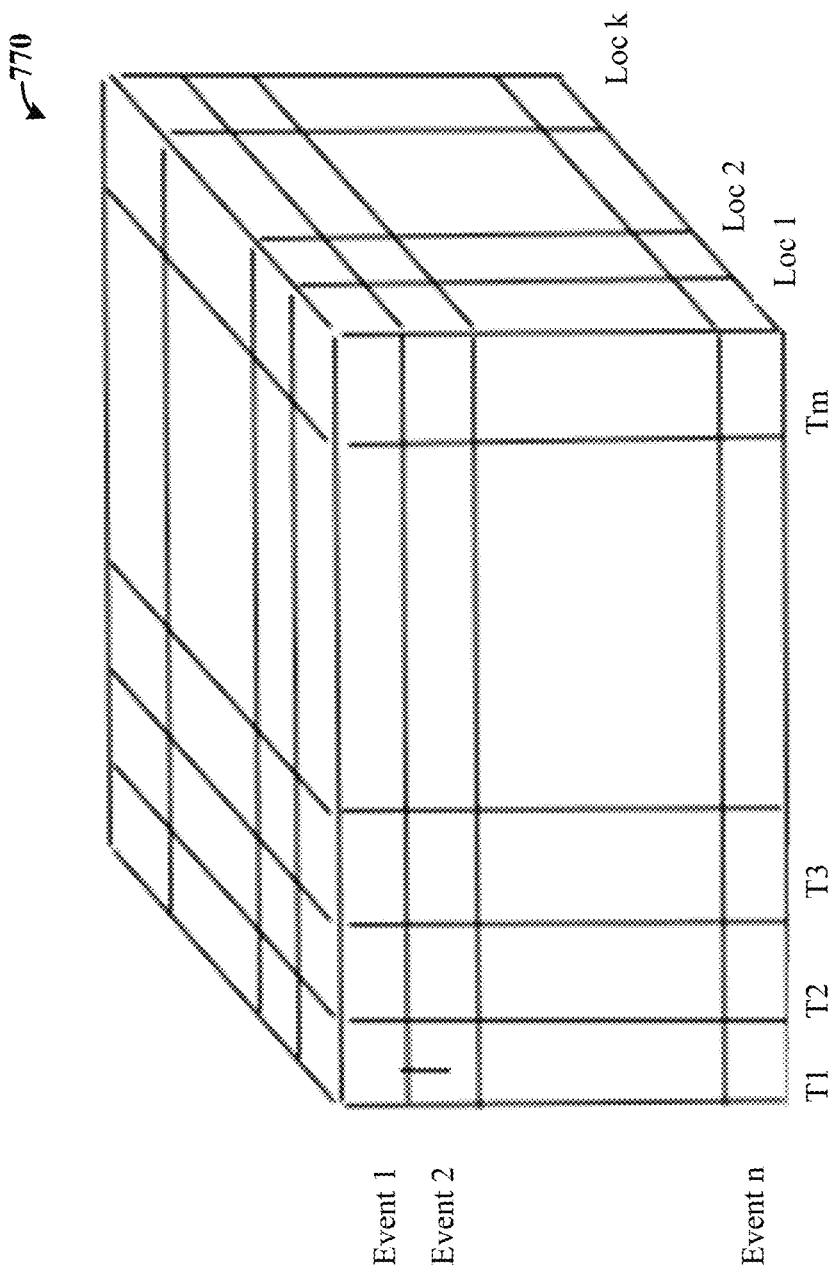
FIG. 7 illustrates an example graphical representation of events leading to a hot flash, in accordance with various embodiments.

Inputs from GPS can be used to form a similar matrix of time-location inputs for the sub-model 2 543-2. When there is a relationship between the calendar events and GPS locations and the occurrence of a hot flash, a 3D data chart can be created where the elements represent a specific event at a specific location and on a specific time, and which can be represented by coordinates, such as illustrated by FIG. 7.

Figure 10:
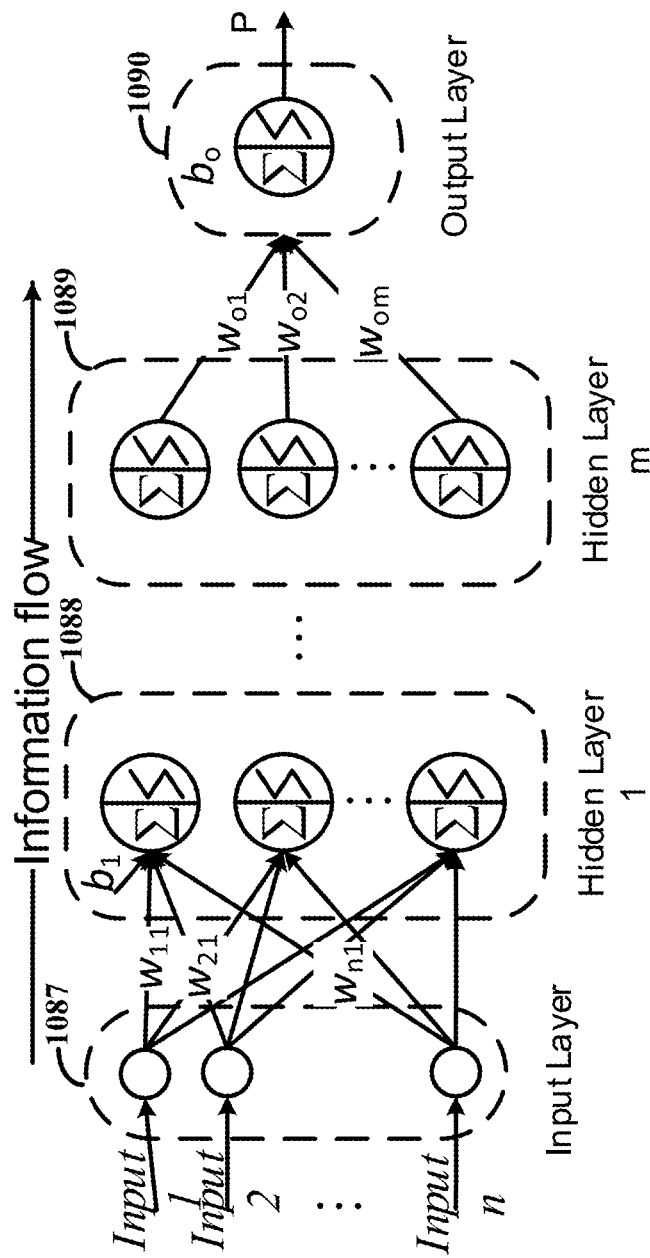
FIG. 10 illustrates an example flow of information within a system, in accordance with various embodiments.

An example third input category for sub-model 3 543-3 can include environmental or atmospheric data, such temperature, humidity, etc. and which can be treated the same way as category 1. In embodiments in which the hot flash probability is to be predicted in the future, the machine learning process may be designed in a way that outputs the hot flash probability in several future time intervals, for example, for every 30 mins. As an example, a similar neural network as shown in FIG. 10 can be adopted. The output layer can consist of a number of outputs each representing the hot flash probability in a specific time interval in the future. The rest of the machine learning, optimization and cost function are the same.

An example fourth input category for sub-model 4 543-4 includes a mood of the user. The mood may be obtained every morning as a part of a self-report, e.g., by a score of 0-10, and are used as inputs for sub-model 4 543-4. The number of hot flashes and/or their severity during that day are used as the target output of the sub-model 4 543-4. The output can be a measure of the severity and or the number of hot flashes during that day. An MLP may be used to model this where the output activation function is a linear function.

The output of the sub-models 543-1, 543-2, 543-4, 543-4 (e.g., P1, P2, P3, P4) designed for each category of inputs are fused to form a final probability P of a hot flash occurrence. A simple example is a weighted summation of the output probabilities of the sub-models 543-1, 543-2, 543-3, 543-4. To find the weights, methods such as regression analysis can be applied. Because the final probability may not be obtained by a linear weighted summation of the sub-models outputs, more advance machine learning methods may be used. Similar machine learning methods described for category 1 can be applied for this purpose. An example is a MLP that accepts the output probabilities of the sub-models and outputs the final probability. Assuming that there are k categories, the system accepts k inputs (k probabilities of hot flash occurrence based on the input type) and output a single value probability P of hot flash occurrence.

Figure 6:
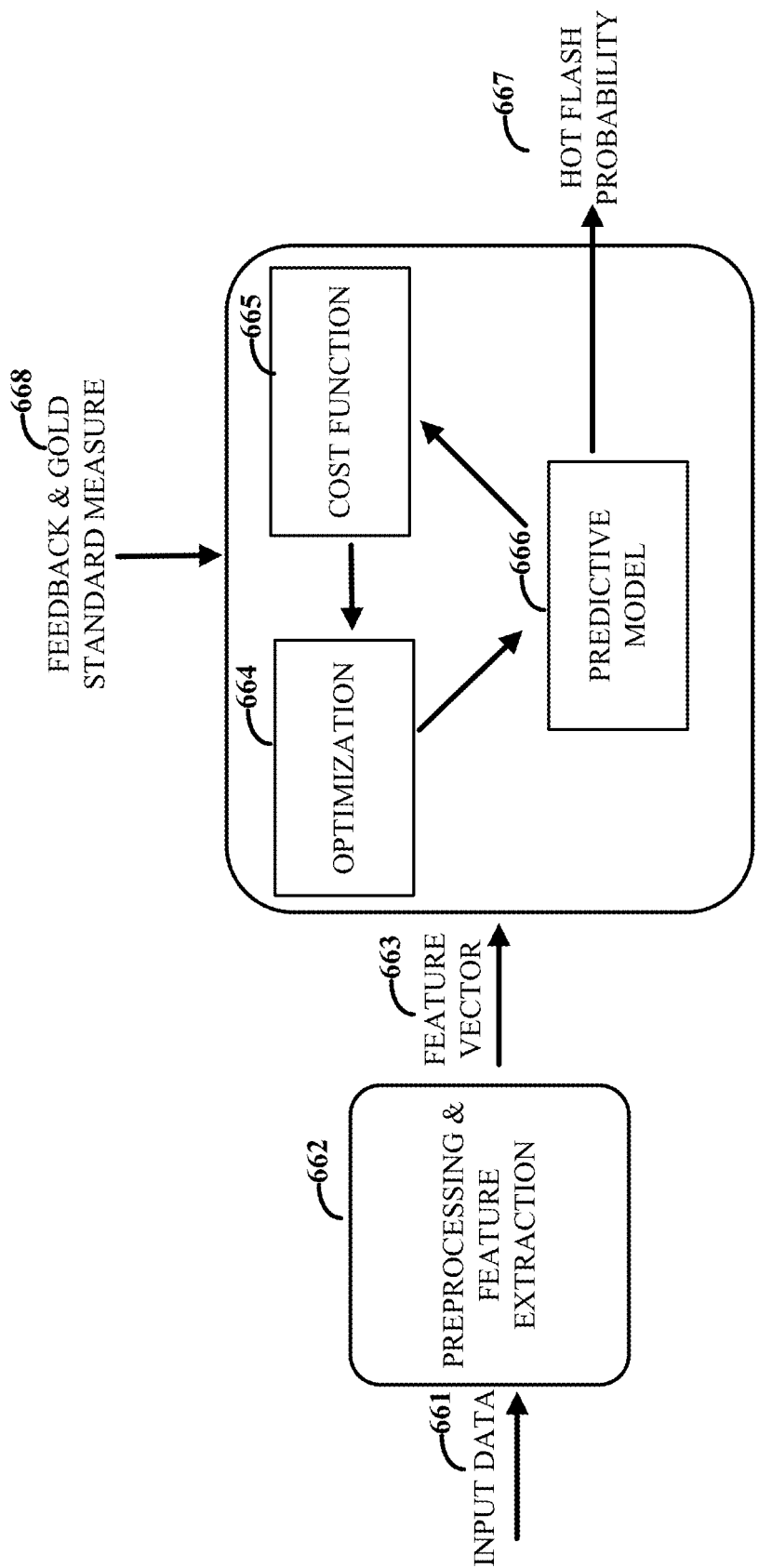
FIG. 6 illustrates another example process for generating a predictive model, in accordance with various embodiments.

FIG. 6 illustrates another example process for generating a predictive model, in accordance with various embodiments. More specifically, the process can be used for generating each of the sub-models or the predictive model illustrated by FIG. 5. As shown, data is input at 661 for preprocessing and feature extraction, at 662. A feature vector is output at 663 and input for performing machine learning to generate the predictive model at 666.

The predictive model gives the probability of the hot flash occurrence based on the observed and/or collected data. A simple example is the logistic regression model which defines a linear decision boundary between the training samples associated with a hot flash occurrence and those that are not. A more complex model can be built when there is a more complex or non-linear relationship between the inputs and output. A deep neural network such as a multi-layer perceptron (MLP) may be used for this purpose. The structure of the MLP with n inputs is shown in FIG. 10, as further described below.

To calculate the optimum network parameters (weights and biases in the case of neural networks), an optimization operation, such as backpropagation, can be used which can be done in batch or incremental styles, at 664. In the batch mode, all available training data are provided to the network to calculate the optimum parameters, while in the incremental style, the parameters are updated each time a training sample is presented to the network.

The optimization of the model parameters is done by minimizing a cost function, at 665. An example of for the cost function is the cross-entropy error which the system defines between the estimated hot flash probabilities and the "true" hot flash distribution. Given a dataset of N training samples the cross-entropy cost function is defined as follows:

$$J = -\sum_{i=1}^{N} t_i \log(y_i) + (1 - t_i)\log(1 - y_i)$$

where ti is the true hot flash probability for training sample i that could be either 0 or 1, Yi is the predicted probability which can take any value between 0 and 1. Minimizing the negative log likelihood cost function is equivalent to maximizing the likelihood of the correct probability.

During training, the cost function is minimized by tuning the model parameters so that the inputs corresponding to a hot flash occurrence results in an output probability of close to 1 and inputs that are not associated with the occurrence of a hot flash results in an output probability of close to 0.

The built model, when fed by new inputs, outputs the probability, at 667, of hot flash occurrence which could vary from 0 to 1. The model is updated over time based on the new user inputs and/or feedback data, at 668, and sensor data regarding the hot flash occurrence and its severity.

Other machine learning models that may be used for this purpose can include naive Bayes, probabilistic decision tree and probabilistic support vector machines classifiers. Other structures of neural networks may also be incorporated such as recurrent neural networks, radial basis neural networks, etc.

FIG. 7 illustrates an example graphical representation of events leading to a hot flash, in accordance with various embodiments. More specifically, FIG. 7 shows a cuboid representation 770 that correlates events leading to the hot flash. Representing the elements of the cube by their coordinates ($t_i$, $event_j$, $loc_k$), the element (i, j, k) is assigned a 1 when event j happens in location k and at time interval i, and 0 unless otherwise. The elements of the 3D chart form the inputs to the analysis module (e.g., the machine learning and/or the predictive model or sub-models). The output of the analysis module can form probability function over the desired time intervals. Since the input dimension may be too high, statistical methods such as principal component analysis may be used to reduce the dimension.

Figure 8:
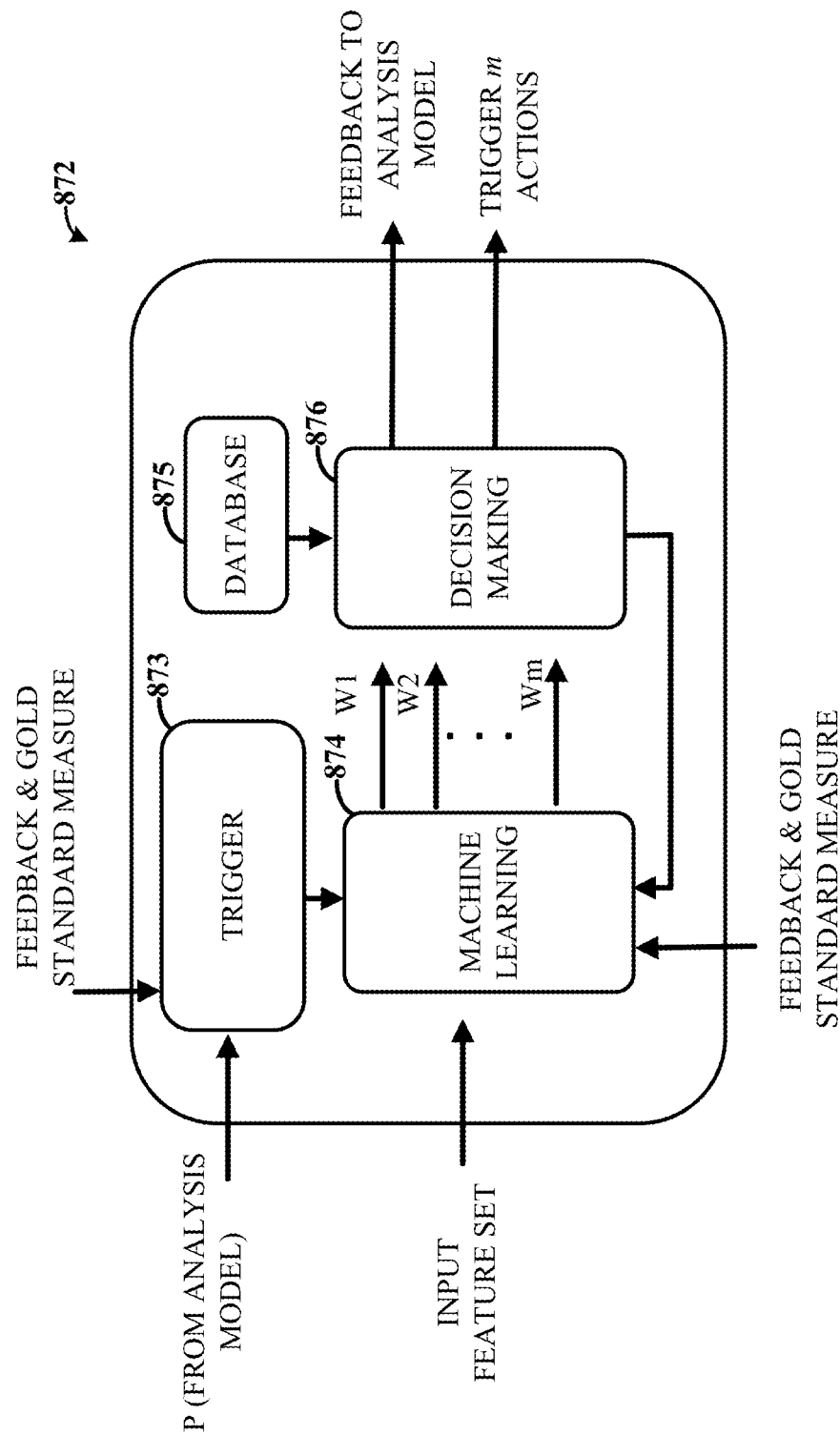
FIG. 8 illustrates another example process for triggering action, in accordance with various embodiments.

FIG. 8 illustrates an example process for triggering action, in accordance with various embodiments. For example, FIG. 8 illustrates a configuration of an actions module 872, such as the actions module 434 illustrated by FIG. 4. Several actions are performed by the actions module 872 that may mitigate or reduce the occurrence of a hot flash or mitigate or reduce their effect on the user. The actions module 872 may output signals that cause specific actions to occur within the vicinity of the user. These actions may be designed to provide relief to the user. An example of such an action is to commence operation of cooling circuit, such as a cooling device. As previously described, the cooling circuitry may be a fan or an air conditioner, among other devices. The actions module 872 may also or alternatively provide suggestions or tips that the user may follow. Examples of tips include relaxation exercises, changes in diet, use of a cooling circuit, etc.

The action may be triggered by one or more thresholds. In the specific example of FIG. 8, a threshold T is set to trigger the actions module according to the final probability P of hot flash occurrence, at 873. When the hot flash probability P exceeds the threshold, the actions module 872 becomes active. The actions module 872 uses machine learning, at 874, to determine the occurrence of a hot flash episode based on prior events and input data. In some embodiments, the actions module 872 is able to provide mitigating output/action a few seconds up to one minute prior to the onset of a hot flash, where the mitigating output/action can last the entire duration of the hot flash and ceases to provide mitigating output/action when certain biological parameters fall below set threshold values.

The actions module 872 contains a database 875 of different actions and tips that can be provided to the user. The actions module 872 receives all the category inputs, as previously described, and weights different actions according to the feedback on the effect of the action taken, which may be user feedback or inferred. As a specific example, the actions are scored by user from 0 to 10 and these scores form the desired weight W of the corresponding action. Machine learning, at 874, can also be used in the actions module 872 to learn from the set of input categories including physiological signals, environmental signals, and different events extracted from the calendar in order to find the best action to be taken at any specific time/occasion/physiological status. The output of the machine learning, at 874, consists of n different weights each corresponding to an action in the action database. The decision-making is performed, at 876, to select m actions/tips with the highest weights to be triggered.

In the absence of the feedback, the performance of the actions is evaluated based on their efficiency in reducing the occurrence of the hot flashes (as determined by a combination of estimate probability of hot flash occurrence and real physiological hot flash event). If a hot flash is expected and did not happen after an action, the action's corresponding weight is set to $P_{final} \times 10$. If a hot flash still occurred the action's corresponding weight is set to 0. The weight of the actions not taken may not be updated.

Because the probability of the occurrence of a hot flash may be affected by the actions module 872, careful consideration is taken when training the machine learning associated with the predictive model, and while the actions initiated by the actions module 872 are also active. In an example, the segments of the data where an actions module 872 is triggered can be excluded from the training set. In another example, feedback signals from the actions module 872 may be sent back to the machine learning as inputs in order to provide them with the accurate information regarding the user status and the actions taken. As another specific example, the input data categories 1 and 3, described in connection with FIG. 5, can receive additional inputs from the actions module 872 representing the actions module's activity. For example, each action can be represented by 1 (as soon as the actions module 872 is used to activate that action) and 0 (as soon as the actions module deactivates the action). Input category 3, e.g., the event time chart, can be updated by adding new events corresponding to the actions taken.

The performance of the actions module 872 is evaluated based on the feedback and the real occurrence of the hot flashes in response to the actions taken. If a specific action was successful in suppressing a hot flash or in general satisfying the user, the threshold T is reduced. If the user is not satisfied with the actions module 872 being triggered, the threshold T may be reduced by a specific value leading to a lower triggering of the actions module 872 and limiting the triggers to when the probability of a hot flash is very high. A very high threshold can eventually not trigger the actions module 872.

The database 875 of actions/tips contains several tips that can be given to the user (relaxation techniques such as deep breathing) and different actions that may be performed to reduce the number of hot flashes or their effect on the subject (cooling therapies). The initial weights of the actions can be set by an expert or set by the user through scoring the actions in the first usage of the system. The machine learning can be used to adjust the action weights based on their effect on the user and their efficiency in reducing the hot flash occurrence or its effect on the user.

Figure 9:
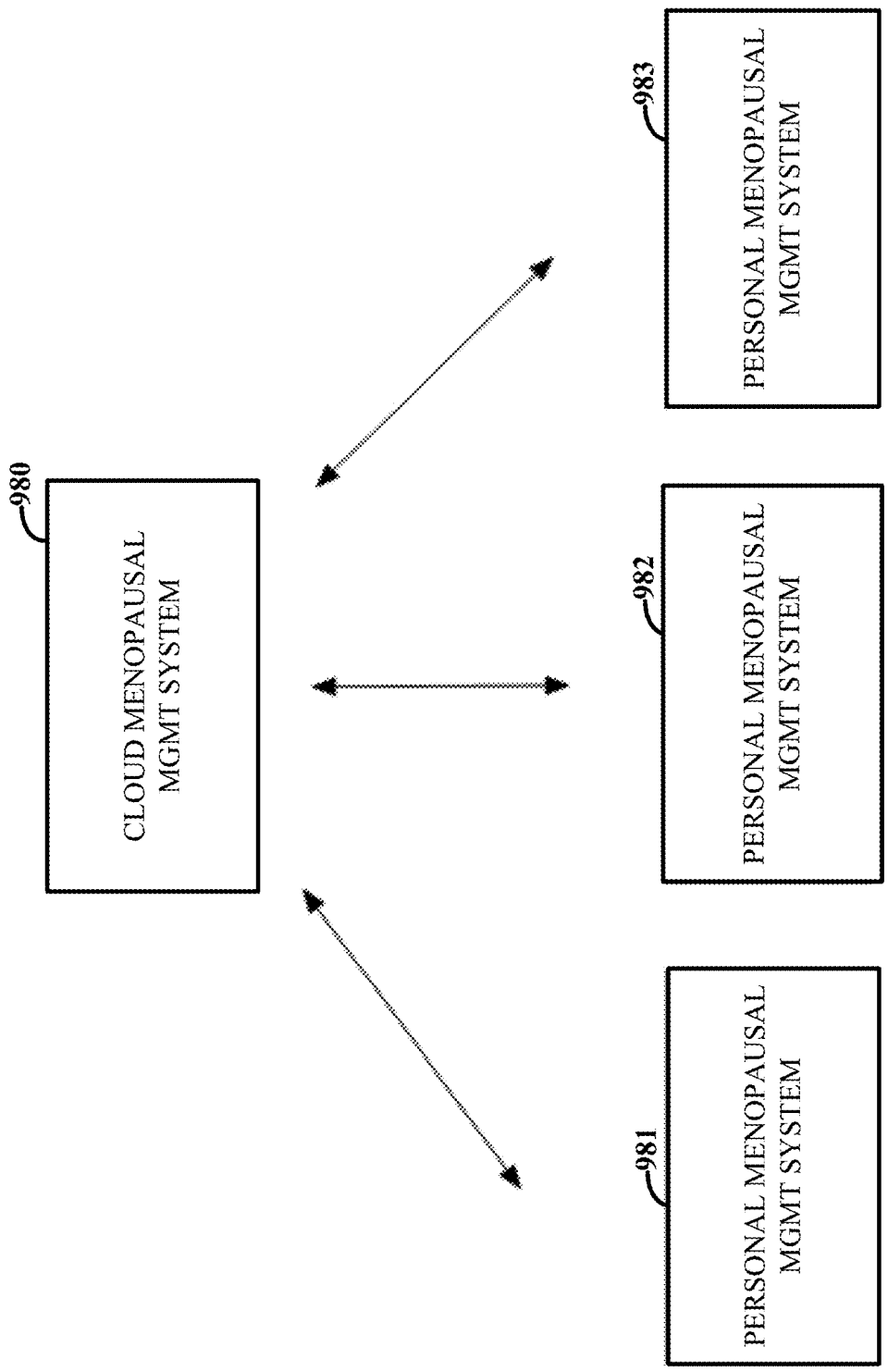
FIG. 9 illustrates an example cloud-based system for hot flash management, in accordance with various embodiments.

FIG. 9 illustrates an example cloud-based system for hot flash management, in accordance with various embodiments. In specific embodiments, a menopausal management system or other hot flash management system can include a plurality of personal menopausal management systems 981, 982, 983 in communication with a cloud-based menopausal management system 980.

The cloud-based menopausal management system 980 may involve a machine learning process and a database. The inputs to this machine learning may include the reports generated by the personal menopausal management systems 981, 982, 983. The machine learning process in the cloud-based menopausal management system 980 may be used to learn hot flash mitigation strategies based on analyzing information from a population of users. It is possible that users share some common characteristic, such as age, or find one or several specific hot flash mitigation strategies that are successful. If such knowledge is gleaned from collecting population data, then that information may then be shared with the individual users, such as via the personal menopausal management systems 981, 982, 983.

FIG. 10 illustrates an example flow of information with a system in accordance with various embodiments. More specifically, FIG. 10 illustrate an example MLP neural network with m outputs, as previously described. The structure of the MLP with n inputs is shown in FIG. 10. Each node in the first hidden layer 1088 computes a weighted summation of the inputs from the input layer 1087 and passes the result to an activation function such as a sigmoid function. The outputs of the first hidden layer 1088 are then fed to the next layer 1089 where another weighted summation is performed and passed through appropriate activation functions. The outputs of the last hidden layer 1089 are weighted and summed and then passed through a logistic activation function in order to outcome a continuous hot flash probability value of 0 to 1 at the output layer 1090.

Figure 11A:
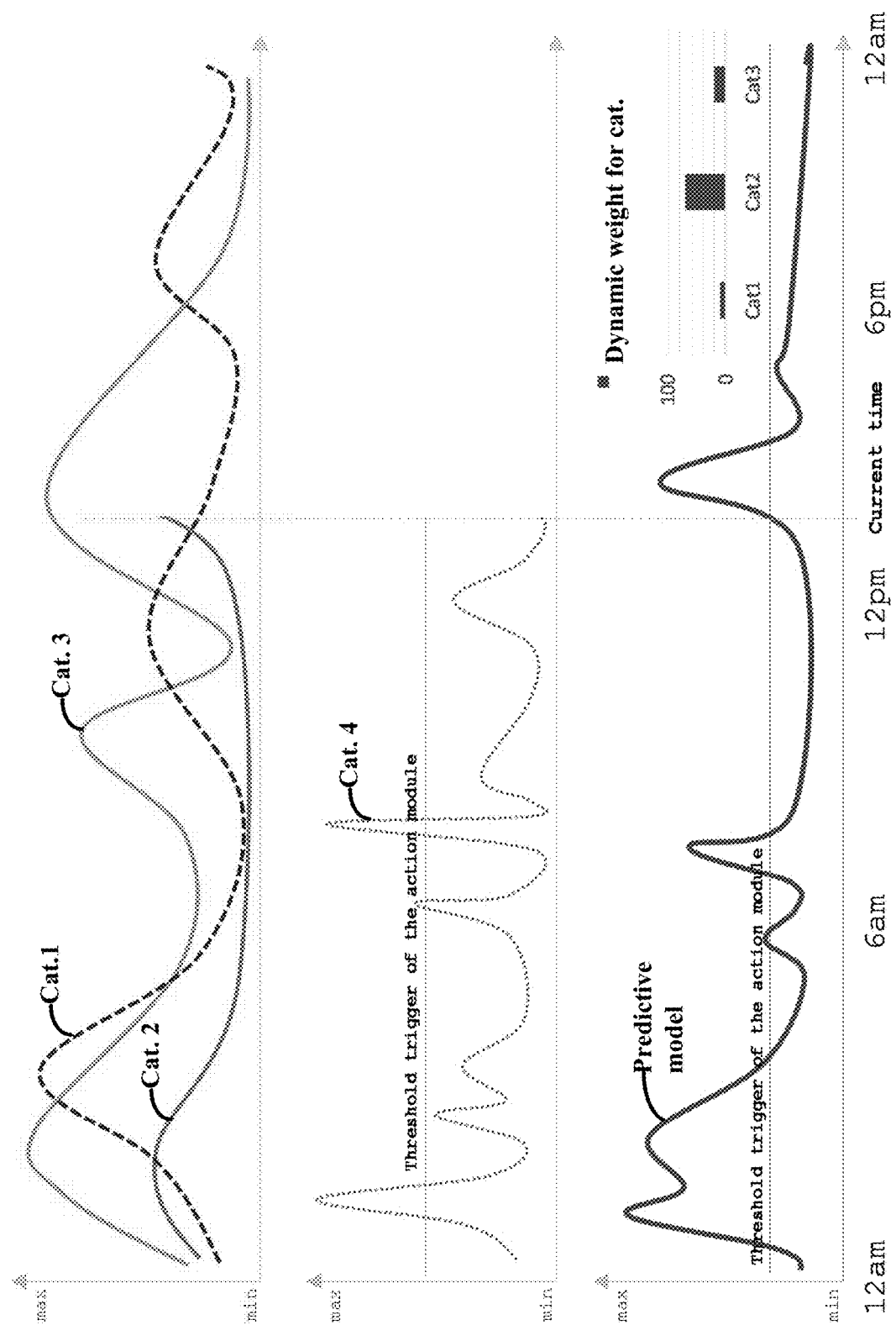
FIGS. 11A-11B illustrate example input data for a predictive model, in accordance with various embodiments.
Figure 11B:
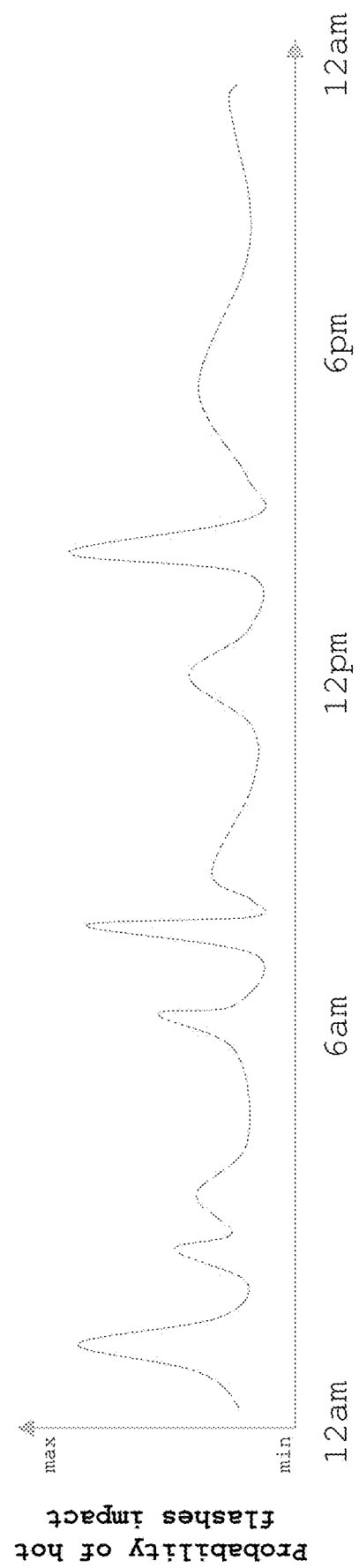

FIGS. 11A-11B illustrate example output data of a predictive model, in accordance with various embodiments. More specifically, FIGS. 11A-11B illustrate different probabilities of a user having a hot flash over time based on the above described different categories of input data. The different input data can be on-line and/or off-line from different sources that indicate a probability of hot flashes. The different categories of data have different weights based on success (e.g., past success for the particular user or other users) in predicting a hot flash occurrence and which can be updated over time. The actions module is triggered based on source of data and the probability exceeding the threshold. In specific embodiments, as shown by the predictive model, the actions module can be triggered a threshold period of time before the probability exceeds the threshold, such that the hot flash is anticipated, mitigated, and/or prevented. Although embodiments are not limited to hot flash mitigation and can be used to mitigate or otherwise manage other symptoms of menopause.

The categories of input data, in the example illustrated by FIG. 11A include a first category of off-line group evidence (e.g., night-time incidence distribution, lunch-time incidence distribution, dinner-time incidence distribution), a second category of on-line user/users' physiological states (e.g., heart rate, heart rate variability, and others), and a third category of on-line user/users' routine (e.g., calendar information, travel, meetings). A fourth category can include on-line user/users' physiological signals pattern of divergence (e.g., heart rate increase coupled with drop of plethysmography waveform amplitude, with a five second resolution). The fourth category may, for example, be used to set the threshold trigger of the actions module. Each of categories 1 through 3 can be dynamically weighted to generate the predictive model indicative of the probability of a hot flash occurrence.

FIG. 11B illustrates an example impact of hot flashes. Similarly to that illustrated by FIG. 11A, the streaming output of the probability of the impact of the hot flash can be generating using the predictive model. For example, a hot flash while the user is exercising may not have as great of a lifestyle and/or physiological impact as compared to when the user is in front of other people (e.g., in a meeting) or is sleeping (e.g., may wake up the user). The action taken by the actions module may be adjusted depending on the impact on the user, which may not be the same at different times of the day. As previously described, the impact or severity may be a scaled parameter.

The above described systems and computer-readable instructions may be used to track various factors of hot flashes for a user and to mitigate the effects of the hot flashes by generating a predictive model which is dynamically updated over time. Based on the dynamic predictive model, the system is used to predict occurrence of a hot flash, to anticipate an imminent hot flash, and to mitigate symptoms caused by hot flashes and/or other symptoms of menopause.

More Detailed/Experimental Embodiments

Embodiments in accordance with the present disclosure include systems and methods involving management of hot flashes or, in specific embodiments, management of menopause symptoms for one or a more users. The following provide specific example uses of the above-described systems.

As a first example, it is assumed that the occurrences of hot flashes are being monitored over some period of time and a table such as Table 1 is internally generated. In this case, through the user interface, the user may ask the question—"Over the last several weeks, when have I had hot flashes". In response, if a table such as Table 1 exists, the system may initiate an analysis of the data and respond through the display module "In the last several weeks, hot flashes have occurred typically during night between the hours of 2 AM and 3 AM".

As a second example, it is assumed that the occurrences of hot flashes are being monitored over some period of time and a table such as Table 2 is internally generated. In the case, through the user interface, the user may ask the question—"Over the last several weeks, when have I had hot flashes and what can I do to minimize such occurrences". In response, if a table such as Table 2 exists, the system may initiate an analysis of the data and respond through the display module "In the last several weeks, hot flashes have occurred typically during night between the hours of 2 AM and 3 AM. Also, if you keep the temperature at 65 F fewer hot flashes seem to occur".

Specific embodiments are directed to a menopause management system. As described above, women approaching menopause are more likely to have trouble sleeping and suffer from insomnia symptoms than at other times of their life. Measurements in a laboratory setting show that perimenopausal women with clinical insomnia are spending a significant time awake during the night (measured with gold standard polysomnographic sensors) and consequently have a shorter night-time sleep period than other women: almost fifty percent of the women have less than six hours of sleep, which puts them at risk for poor health. Nocturnal hot flashes are a centerpiece in the insomnia problems that midlife women report. Various experimental data shows that approximately seventy percent of hot flashes are associated with an awakening (as measured objectively with sensors) and once a subject is woken up with a hot flash, the subject may not be able to go back to sleep immediately and thus sleep is interrupted.

Figure 12:
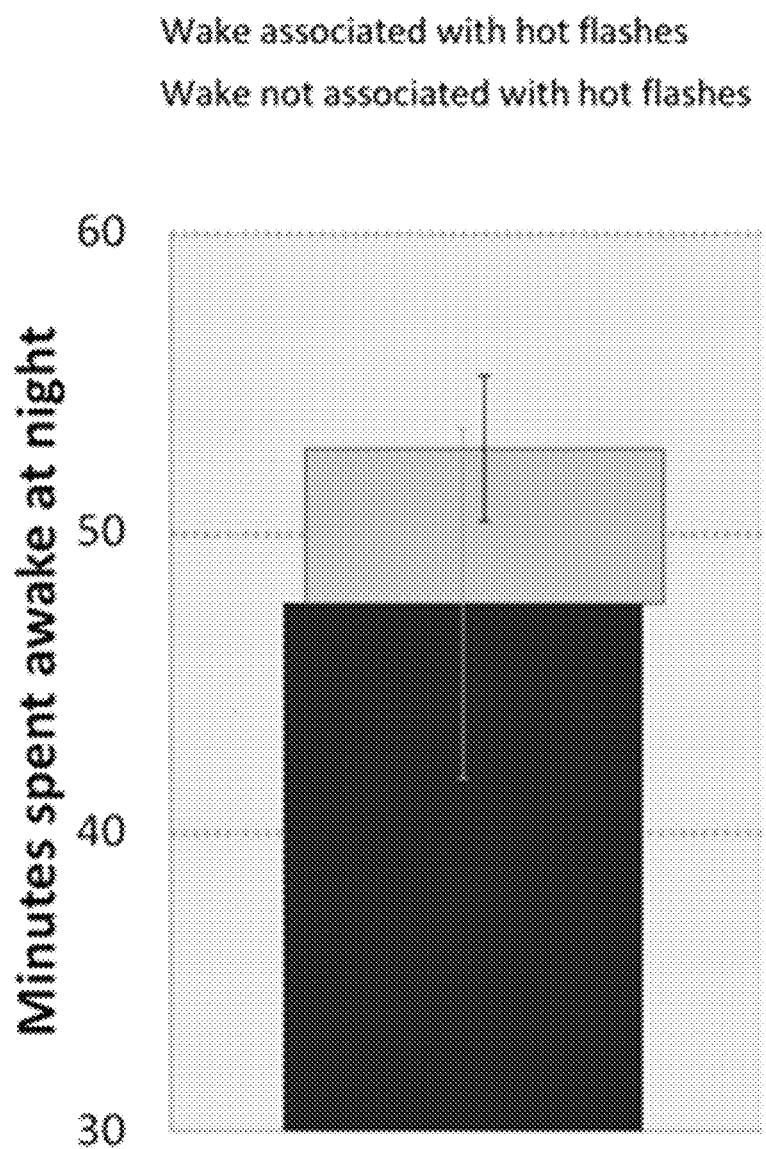
FIG. 12 illustrates an example graphical representation of the amount of wake time associated with hot flashes and not associated with hot flashes, in accordance with various embodiments.

FIG. 12 illustrates an example graphical representation of the amount of wake time associated with hot flashes and not associated with hot flashes, in accordance with various embodiments.

Everyone wakes up intermittently across the night (recorded using sensors) even if they are not always aware of it. Women who have hot flashes have "an extra load" on their wake system. The prevalence of hot flashes occurs commonly during sleep. In general, the presence of hot flashes adds additional wake time to the subjects' overall time spent awake during the night. Systems in accordance with the present disclosure can reduce the amount of hot flash awake time for a user, such as during the night. Given that sleep complaints and hot flashes are linked with functional impairment, poor quality of life, decreased work productivity, and increased healthcare use, reducing hot flash impact on sleep can lead to a better quality of life.

Figure 13:
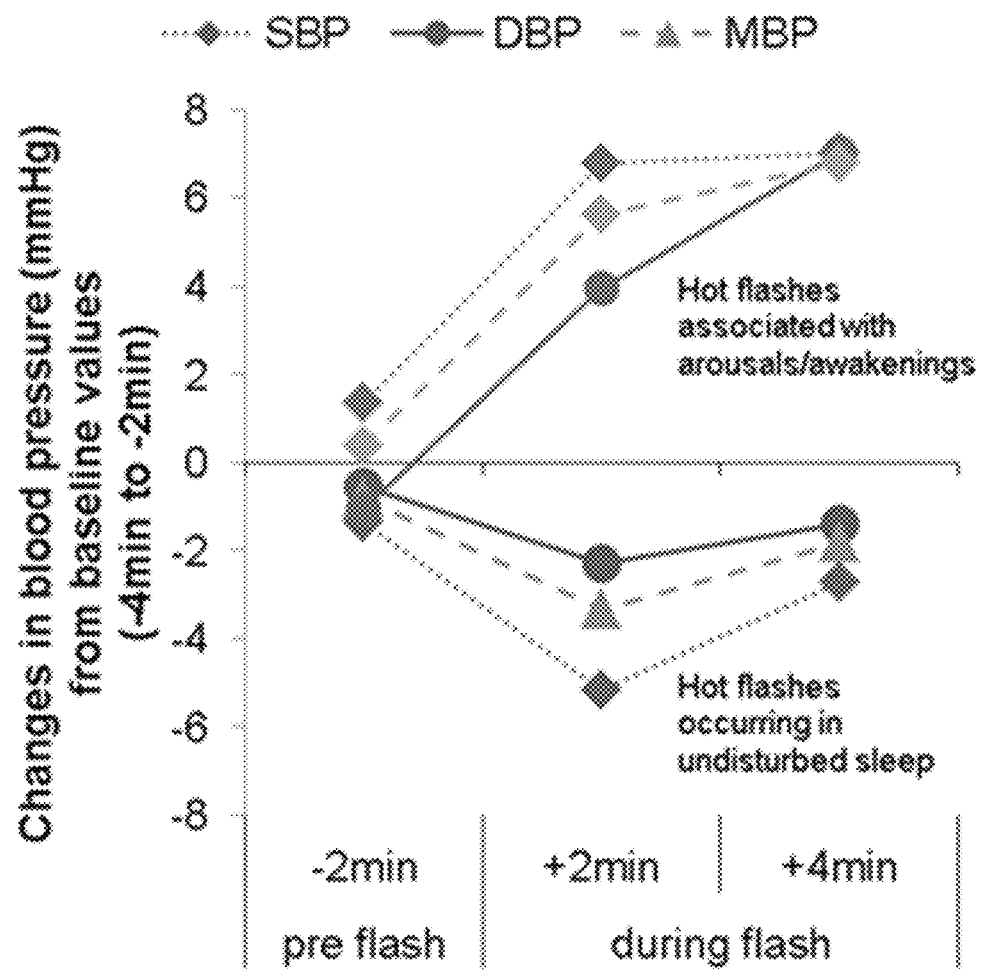
FIG. 13 illustrates an example graphical representation of the correlation of blood pressure changes to occurrences of a hot flash, in accordance with various embodiments.

FIG. 13 illustrates an example graphical representation of the correlation of blood pressure changes to occurrences of a hot flash, in accordance with various embodiments. Hot flashes that are combined with an awakening are associated with a strong cardiovascular activation—both heart rate and blood pressure can increase.

More specifically, FIG. 13 shows systolic blood pressure (SBP), mean blood pressure (MBP), and diastolic blood pressure (DBP) just before and during a hot flash. As the graph shows, both the SBP and the DBP increase at two minutes into a hot flash and remain high at four minutes into the hot flash. It is possible that repeated cycles of hot flash-wake periods across the night, and across many nights can take a toll on the cardiovascular system, disrupting the restorative function of sleep on the cardiovascular system. Additionally, having multiple hot flashes during the night is associated with more self-reported wake-time, even after controlling for other factors that can impact sleep, such as anxiety and stress. Women classified hot flashes ranging from warm to feverish and intense, and perceive them across their whole body most of the time. They report hot flashes during the night as bothersome (49.8%), annoying (41.6%), and irritating (34.7%), and disruptive to sleep. It may be inferred from the above description that hot flashes have a demonstrable effect on women' health and quality of life. Various embodiments as described above are directed to a system that can calculate the instantaneous probability of a hot flash occurring. With this data, a user and/or the system may take appropriate steps to mitigate the effect of hot flashes and/or other menopause symptoms on the user.

Studies in awake women having hot flashes show that vasodilation is mediated by a transient increase in skin sympathetic nerve activity and is accompanied by increased heart rate (HR) and decreased mean arterial pressure. It has also been shown that hot flashes are markers of higher risk of subclinical cardiovascular (CV) disease. Specifically, presence and/or severity of hot flashes has been associated with higher blood pressure (BP), poorer endothelial function and flow-mediated dilation, more aortic calcification, and higher carotid intima media thickness, with some relationships being stronger in women with an early onset of heat flashes. Women with heat flashes are also more likely to have an adverse adipokine profile, higher lipid and lipoprotein levels, insulin resistance, and possibly increased risk for subsequent CV disease events. Various embodiments can be used to study the underlying mechanisms linking hot flashes with markers of subclinical CV risk and the hot flashes alone may be just one indicator of underlying risk.

A factor that may contribute to increased CV risk in women with multiple hot flashes is hot flashes-related sleep disturbance. Sleep and the CV system are intimately connected, with sleep providing an overall reduction in CV effort (decreases in BP, HR, cardiac output) across sleep. Arousal from sleep can disrupt the reduction in CV effort, which is a pathway to adverse CV health. Higher nocturnal BP is a strong predictor of adverse CV events in hypertensive and general populations, and is associated with reduced endothelial function.

Hot flashes are associated with poorer sleep quality and chronic insomnia, and women reporting moderate-severe hot flashes are almost three times more likely to report frequent nocturnal awakenings compared to women without hot flashes. Physiological hot flashes may be identified by a sudden increase in sternal skin conductivity due to increased sweating, and are associated with more objectively identified awakenings, greater wake time, and/or more stage N1 (light) sleep.

It has been identified that there are different patterns of CV changes across nocturnal hot flashes, depending on their association with or without arousal/awakening from sleep. When hot flashes are associated with sleep disturbance, BP shows a sustained increase, which can dampen nocturnal CV recovery in women with multiple hot flash-wake events, ultimately increasing risk for CV disease. Indeed, it has been identified that the nocturnal BP profile is altered in women in the menopausal transition with insomnia disorder, who were more likely to have hot flashes than controls. It is believed that hot flashes associated with sleep disruption are associated with a greater CV response compared to hot flashes in undisturbed sleep. Other user characteristics (e.g., menopausal stage, age, depression symptoms), and sleep stage and time of night in which the heat flash occurred, are used to predict the likelihood of hot flash-associated sleep disruption.

Figure 14:
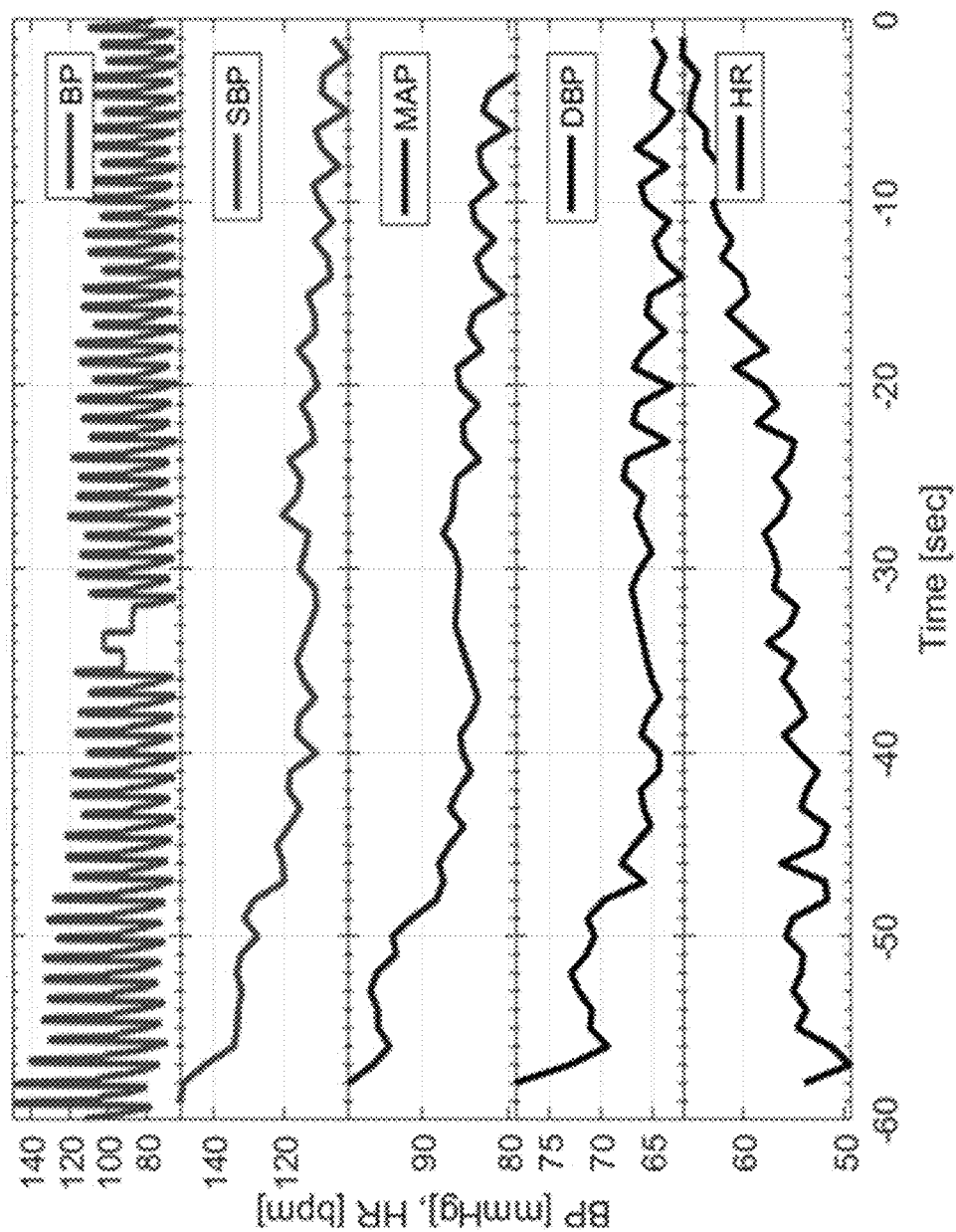
FIG. 14 illustrates an example graphical representation of the correlation of beat-to-beat changes in physiology to occurrences of a hot flash, in accordance with various embodiments.

FIG. 14 illustrates an example graphical representation of the correlation of beat-to-beat changes in physiology to occurrences of a hot flash, in accordance with various embodiments. More specifically, the beat-to-beat changes in physiology, such as a decrease in blood pressure and increase in heart rate prior to (e.g., right before) the hot flash as shown by FIG. 14 which illustrates blood pressure (BP), SBP, mean arterial pressure (MAP), DBP, and HR measurements just before a hot flash.

Various systems, as described above, can utilize the different patterns of CV changes across nocturnal heat flashes. The system can include inputs of BP, HR, skin conductance and other physiological parameters for predicting and/or anticipating a hot flash. For particular users, the system can identify that when hot flashes are associated with sleep disturbance, BP shows a sustained increase, which can dampen nocturnal CV recovery in women with multiple hot flash-wake events, ultimately increasing risk for CV disease.

Hot flash characteristics beyond frequency can be useful for predicting future hot flashes, including amount of hot flash-associated wakefulness, age when heat flashes emerge, and hot flash trajectory patterns across the menopausal transition.

A small number of hot flashes occur without any sleep disturbance; for these hot flash events, HR is higher before the rise in skin conductance, and remains higher than baseline for the duration of the hot flash, similar to what happens across hot flashes recorded when women are awake. Also, PEP is shorter, and cardiac vagal activity declines, during sleep hot flashes. Taken together, this suggests that increased HR during a heat flash is mediated by a combination of cardiac vagal withdrawal and cardiac sympathetic activation. In addition, blood pressure declines across undisturbed hot flashes (and similarly for hot flashes recorded when women are awake and immobile during the daytime), probably due to a decrease in total peripheral resistance associated with increased blood flow, particularly to the cutaneous vessels to dissipate heat, which may be evident even before a rise in skin conductance. The drop in BP probably triggers a baroreflex response to increase HR (beyond the initial HR increase when a heat flash is triggered) such that HR continues to be higher during recovery periods, but BP returns to baseline. The CV response to a hot flash in undisturbed sleep, therefore, represents a normal thermoregulatory response and is similar to responses to hot flashes while awake.

Sometimes, for nocturnal hot flashes, the awakening lags the hot flash onset. Examination of CV measures around these hot flashes shows components of the other two heat flash categories: an initial change associated with hot flash-onset (increase in HR and drop in BP, reflecting a heat dissipation response), and the subsequent changes associated with an awakening (increase in HR and BP). Possibly, arousal hot flashes have a more intense trigger, causing arousal at the same time as hot flash onset, whereas for delayed arousal hot flashes, the initial intensity may not be so strong, yet, a woman may wake up following the cascade of changes that characterize a hot flash (sweating, change in skin blood flow and temperature, drop in BP).

Other factors that determine likelihood of an arousal from sleep include sleep stage and sleep depth, stimulus modality, and individual characteristics (like age), and these factors can be used by the system to determine an impact of the hot flash, such as illustrated by FIG. 11B. Sleep hot flashes were more likely to arise in N3 sleep. N3 (slow wave sleep) is associated with a higher arousal threshold to auditory stimuli, and there may be a similarly higher arousal threshold to hot flashes. Sleep hot flashes were more likely to arise in REM sleep, which could be due to lower awakening responsiveness in REM sleep and/or the potentially lower sensitivity of the thermoregulatory system, and associated decrease in sweating responses, during REM sleep. Any hot flashes that do occur in REM sleep may be less intense (i.e. less likely to be associated with an awakening/arousal) than those in other sleep stages. Older age was associated with greater likelihood of having hot flash-associated sleep disturbance, which may be due to lower awakening thresholds in older adults. It is also possible that as women have more hot flashes over time, they may become more sensitized to hot flash-associated arousal; or the hot flashes may be more severe in older women.

Various embodiments are implemented in accordance with the underlying Provisional Application (Ser. No. 62/694,946), entitled "Menopause Management System," filed Jul. 6, 2018, to which benefit is claimed and which are both fully incorporated herein by reference for their general and specific teachings. For instance, embodiments herein and/or in the provisional application may be combined in varying degrees (including wholly). Reference may also be made to the experimental teachings and underlying references provided in the underlying provisional application. Embodiments discussed in the Provisional Application are not intended, in any way, to be limiting to the overall technical disclosure, or to any part of the claimed disclosure unless specifically noted.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as"/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values),+/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The skilled artisan would recognize that various terminology as used in the Specification (including claims) connote a plain meaning in the art unless otherwise indicated. As examples, the Specification describes and/or illustrates aspects useful for implementing the claimed disclosure by way of various circuits or circuitry which may be illustrated as or using terms such as blocks, modules, device, system, unit, controller, and/or other circuit-type depictions (e.g., reference numerals 431-436 of FIG. 4 depict a block/module as described herein). Such circuits or circuitry are used together with other elements to exemplify how certain embodiments may be carried out in the form or structures, steps, functions, operations, activities, etc. For example, in certain of the above-discussed embodiments, one or more modules are discrete logic circuits or programmable logic circuits configured and arranged for implementing these operations/activities, as may be carried out in the approaches shown in FIG. 5-6. In certain embodiments, such a programmable circuit is one or more computer circuits, including memory circuitry for storing and accessing a program to be executed as a set (or sets) of instructions (and/or to be used as configuration data to define how the programmable circuit is to perform), and an algorithm or process as described at FIG. 10 is used by the programmable circuit to perform the related steps, functions, operations, activities, etc. Depending on the application, the instructions (and/or configuration data) can be configured for implementation in logic circuitry, with the instructions (whether characterized in the form of object code, firmware or software) stored in and accessible from a memory (circuit).

Various embodiments described above, may be implemented together and/or in other manners. One or more of the items depicted in the present disclosure can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

What is claimed is:

1. A system, comprising:
   sensor circuitry, including a communication circuit, to obtain a physical measurement associated with a user and to communicate the physical measurement, the physical measurement including at least one of heart rate, skin conductance, and blood pressure; and
   logic circuitry to:
   train a predictive model using training data including a plurality of input parameters and dates and times of reported hot flashes to identify a plurality of patterns of the input parameters and the reported hot flashes and to indicate a probability of the user having a hot flash at a date and time, wherein:
      the plurality of input parameters is selected from a group consisting of: calendar or schedule data, lifestyle data, environmental data, health information including a plurality of physical measurements, and combinations thereof;
      the plurality of physical measurements includes heart rate, skin conductance, and blood pressure; and
      the plurality of patterns includes different patterns having different weights and being associated with the reported hot flashes and respectively with input parameters of physiological signals, calendar or schedule data, and environmental data;
   apply the trained predictive model to additional received input parameters associated with the user to identify the probability of a hot flash occurrence at the date and time;
   revise the probability based on the physical measurement received from the sensor circuitry using the trained predictive model; and
   in response to the revised probability being outside at least one threshold, wherein the at least one threshold is indicative of a hot flash that is predicted to occur or to imminently occur for the user, communicate data indicative of an action to proactively mitigate or prevent the hot flash that is predicted to occur or to imminently occur.

2. The system of claim 1, wherein the system is a menopause management system, the data communicated includes an instruction to activate cooling circuitry, the system further including the cooling circuitry, having a communication circuit and heat transfer circuitry, to provide the cooling to the user in response to the instruction and in advance of an occurrence of the hot flash to proactively mitigate or prevent the hot flash as predicted, and
   wherein at least a portion of the plurality of patterns the predictive model is trained to identify include different patterns of cardiovascular changes identified as being associated with nocturnal hot flashes that cause sleep disturbance and nocturnal hot flashes associated with undisrupted sleep.

3. The system of claim 1, wherein the sensor circuitry includes a wearable physiological sensor to sense the physical measurement including a plurality of physiological signals from the user, and another sensor to sense an atmospheric measurement, and the revised probability being outside the threshold indicates that the hot flash is imminent for the user and anticipates the hot flash prior to the hot flash occurring, wherein the plurality of physiological signals includes the heart rate, the skin conductance, and the blood pressure obtained from the user by the sensor circuitry.

4. The system of claim 1, wherein the logic circuitry is to receive the plurality of input parameters, the input parameters comprising the reported hot flashes for the user and other users, schedule or calendar data, stress level, general mood, dietary data, health information, exercise data, sleep data, and a combination thereof, and wherein the predictive model is trained using machine learning and the plurality of input parameters as inputs and the reported hot flashes for the user and for other users as outputs.

5. The system of claim 1, wherein the physical measurement obtained by the sensor circuitry comprises a physiological signal, atmospheric measurement, motion data, and global position data, and the logic circuitry communicates data indicative of the action includes communicating a message to the user to take the action to mitigate a hot flash.

6. The system of claim 1, wherein the predictive model is trained based on machine learning and includes a plurality of sub-models that each indicate the probability of the user having the hot flash, each of the plurality of sub-models being associated with a pattern of a particular input parameter of the plurality and dates and times of the reported hot flashes and having an associated weight, wherein:
   a first sub-model of the plurality is associated with a pattern of physiological signals including skin conductance, blood pressure, and heart rate and the reported hot flashes;
   a second sub-model of the plurality is associated with a pattern of calendar or schedule data and the reported hot flashes; and
   a third sub-model of the plurality is associated with a pattern of environmental data and the reported hot flashes.

7. The system of claim 6, wherein the sub-models include different patterns of hot flashes for the user based on the particular input parameter and the probability of the hot flash occurrence at the date and time is based on a summation of output probabilities of the plurality of sub-models as weighted by the associated weights.

8. The system of claim 1, wherein the logic circuitry is configured to:
   revise the trained predictive model over time based on feedback data indicative of experienced hot flashes for the user including adjusting weights of the trained predictive model associated with respective input parameters of the plurality based on the feedback data, wherein the feedback data includes at least one of:
  scaled parameters indicative of an impact of each of the experienced hot flashes;
  confirmation of occurrence of the experienced hot flashes based on at least the physical measurement from the sensor circuitry and user input; and
  actions that mitigate the experienced hot flashes; and
adjust at least one of an amount and sensitivity of the physical measurement in response to the revised probability being outside the threshold.

9. The system of claim 8, wherein the feedback data is indicative of a body location of the experienced hot flashes.

10. The system of claim 1, wherein the logic circuitry provides an instruction to the sensor circuitry to increase an amount of the physical measurement obtained by the sensor circuitry or a sensitivity of the sensor circuitry to obtain the physical measurement from a first value to a second value in response to the probability being outside another threshold and within the threshold and wherein the action is predicted to mitigate or prevent occurrence of the hot flash that is predicted or imminent and predicted to decrease a probability of the user waking up at night during a nocturnal hot flash.

11. The system of claim 1, wherein logic circuitry is to:
  train the predictive model to identify the patterns of input parameters including different patterns of cardiovascular changes including changes in heart rate, changes in blood pressure, and changes in skin conductance, that occur together, and which are associated with nocturnal hot flashes that cause sleep disturbance and are associated with nocturnal hot flashes associated with undisrupted sleep; and
  quantify a contribution of hot flashes to an amount of wakefulness during a night.

12. The system of claim 11, wherein the logic circuitry is configured to identify the nocturnal hot flashes associated with sleep disturbance and the nocturnal hot flashes associated with undisturbed sleep based on the different patterns of cardiovascular changes including the changes in blood pressure, the changes in heart rate, and the changes in skin conductance, wherein the different patterns include:
  an increase in heart rate, a decrease in blood pressure, and an increase in skin conductance that correlates with the nocturnal hot flashes associated with undisrupted sleep;
  an increase in heart rate, an increase in blood pressure, and an increase in skin conductance that correlates with the nocturnal hot flashes associated with sleep disturbance; and
  an increase in heart rate, a decrease in blood pressure, and an increase in skin conductance followed by a further increase in heart rate and an increase in blood pressure that correlates with nocturnal hot flashes associated with a delayed awakening and sleep disturbance.

13. The system of claim 11, wherein the logic circuitry is configured to determine an impact of the hot flash that is predicted to occur or to imminently occur for the user based on a likelihood of arousal of the user from sleep and the different patterns of changes in heart rate, changes in blood pressure, and changes in skin conductance.

14. A non-transitory computer-readable storage medium comprising instructions that when executed cause a processor of a computing device to:
  receive a plurality of input parameters indicative of hot flash factors for a user and other users, the plurality of input parameters including reported hot flashes, calendar or schedule data, lifestyle data, environmental data, and health information including a plurality of physical measurements;
  generate a predictive model to indicate a probability of the user having a hot flash at a date and time based on the plurality of input parameters and dates and times of the reported hot flashes, wherein: the predictive model is trained to identify a plurality of patterns of the input parameters as correlated with occurrences of hot flashes, and
    the plurality of patterns includes different patterns having different weights and being associated with the reported hot flashes and respectively with input parameters of physiological signals, calendar or schedule data, and environmental data;
  identify the probability of the user having the hot flash at the date and time using the predictive model and additionally received input parameters;
  revise the probability based on a physical measurement of the user, received from sensor circuitry, using the predictive model;
  in response to the revised probability being outside at least one threshold,
    predict the hot flash is to occur or is imminent for the user, wherein the at least one threshold is indicative of a predicted hot flash or an imminent hot flash;
    increase at least one of an amount of the physical measurement obtained by the sensor circuitry and a sensitivity of the sensor circuitry to obtain the physical measurement from a first value to a second value; and
  communicate data indicative of an action in response to the prediction of the hot flash, the action being based on prior user response.

15. The non-transitory computer-readable storage medium of claim 14, wherein the communicated data is an instruction that activates cooling circuitry worn by the user, in response to the activation, provides cooling to the user to mitigate or prevent the hot flash that is predicted or imminent.

16. The non-transitory computer-readable storage medium of claim 15, wherein the instructions are further executed to generate another instruction to deactivate the cooling circuitry worn by the user in response to a further revised probability, based on an additionally received physical measurement, being within the threshold using the predictive model.

17. The non-transitory computer-readable storage medium of claim 14, wherein the instructions to generate the predictive model are executed to:
  train the predictive model using training data including the plurality of input parameters and dates and times of the reported hot flashes to identify the plurality of patterns of the input parameters and the reported hot flashes, wherein at least a portion of the plurality of patterns include different patterns of cardiovascular changes identified as being associated with nocturnal hot flashes that cause sleep disturbance and nocturnal hot flashes associated with undisrupted sleep;
  apply the trained predictive model to the additionally received input parameters associated with the user to identify the probability of the user having the hot flash at the date and time, wherein the additionally received input parameters include physical measurements including heart rate, skin conductance, and blood pressure; and revise the trained predictive model based on additional input parameters received over time, wherein the trained predictive model is associated with a plurality of thresholds, including the at least one threshold, and wherein the plurality of thresholds is associated with and cause different actions to occur via communication of data indicative of the different actions.

18. The non-transitory computer-readable storage medium of claim 14, wherein the instructions are further executed to provide an instruction to the sensor circuitry to increase the at least one of the amount of the physical measurement obtained by the sensor circuitry and the sensitivity of the sensor circuitry in response to the probability being outside another threshold and within the threshold, wherein the probability being outside the other threshold indicates the predicted hot flash for the user and the probability being outside the threshold indicates the imminent hot flash for the user.

19. A system, comprising:
sensor circuitry, including a communication circuit, to obtain a physical measurement from a user and to communicate the physical measurement, the physical measurement including at least one of heart rate, skin conductance, and blood pressure;
logic circuitry to:
train a predictive model using machine learning and training data including a plurality of input parameters and dates and times of reported hot flashes for a plurality of users including the user to identify a plurality of patterns of the input parameters and occurrences of the reported hot flashes, wherein:
the trained predictive model is indicative of a probability of the user having a hot flash at a date and time based on the plurality of input parameters and weights associated with the plurality of input parameters,
the plurality of input parameters includes calendar or schedule data, lifestyle data, environmental data, and health information including a plurality of physical measurements including heart rate, skin conductance, and blood pressure; and
the plurality of patterns includes different patterns having different weights and being associated with the reported hot flashes and respectively with input parameters of physiological signals, calendar or schedule data, and environmental data;
apply the trained predictive model to additionally received input parameters associated with the user to identify the probability of a hot flash occurrence at the date and time;
revise the probability based on the physical measurement received from the sensor circuitry using the trained predictive model;
in response to the revised probability being outside at least one threshold that is indicative of a hot flash that is predicted to occur or to imminently occur for the user,
communicate an instruction to the sensor circuitry to increase at least one of an amount of the physical measurement obtained by the sensor circuitry and a sensitivity of the sensor circuitry to obtain the physical measurement from a first value to a second value; and
communicate an instruction to cooling circuitry to proactively mitigate or prevent the hot flash predicted to occur; and
the cooling circuitry, including a communication circuit and heat transfer circuitry, to provide at least one of cooling and a sensation of cooling to the user in response to the instruction from the logic circuitry.

20. The system of claim 19, wherein the sensor circuitry includes a wearable physiological sensor to sense a physiological signal from the user that is associated with the physical measurement and another sensor to sense an atmospheric measurement, and the cooling mitigates the hot flash for the user and is provided prior to the hot flash occurring in response to the revised probability being outside the at least one threshold, and
wherein at least a portion of the plurality of patterns include different patterns of changes in heart rate, changes in blood pressure, and changes in skin conductance, which are associated with nocturnal hot flashes that cause sleep disturbance and nocturnal hot flashes associated with undisrupted sleep.

21. The system of claim 19, wherein the sensor circuitry includes a plurality of sensors to obtain different physical measurements including the physical measurement and the cooling circuitry includes a plurality of wearable cooling devices located at different physical locations of the user, wherein the logic circuitry is to predict when the hot flash is to occur or is imminent for the user in response to the revised probability being outside the threshold, and in response to the prediction, communicate the instruction to the cooling circuitry, wherein the different physical measurements include heart rate, blood pressure, and skin conductance associated with the user.

22. The system of claim 21, wherein the logic circuitry further identifies which of the plurality of wearable cooling devices to communicate the instruction to based on the trained predictive model, and
wherein the logic circuitry is to train the predictive model by:
analyzing the plurality of input parameters as inputs and the reported hot flashes as outputs to the predictive model to identify patterns of input parameters as conditions associated with the reported hot flash;
providing different weights to the input parameters based on the identified patterns; and
optimizing the predictive model using a cost function, the inputs, the outputs, and the different weights.

23. The system of claim 19, wherein:
the sensor circuitry is to obtain and communicate additional physical measurements during application of the cooling;
the logic circuitry is to further revise the probability based on the additional physical measurements, and to communicate another instruction to the cooling circuitry in response to the further revised probability falling below the threshold, wherein the further revised probability failing below the threshold indicates the hot flash is complete; and
in response the other instruction, the cooling circuitry is to discontinue providing the cooling to the user.

* * * * *